United States Patent
Yamamoto

(10) Patent No.: US 12,243,128 B2
(45) Date of Patent: Mar. 4, 2025

(54) CONTROL DEVICE, OPERATION METHOD OF CONTROL DEVICE, AND OPERATION PROGRAM OF CONTROL DEVICE

(71) Applicant: FUJIFILM Corporation, Tokyo (JP)

(72) Inventor: Hiroaki Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 352 days.

(21) Appl. No.: 17/829,856

(22) Filed: Jun. 1, 2022

(65) Prior Publication Data

US 2022/0292740 A1  Sep. 15, 2022

Related U.S. Application Data

(63) Continuation of application No. PCT/JP2020/038538, filed on Oct. 12, 2020.

(30) Foreign Application Priority Data

Dec. 11, 2019 (JP) .................. 2019-223581

(51) Int. Cl.
*G01B 9/02091* (2022.01)
*G01B 9/021* (2006.01)
(Continued)

(52) U.S. Cl.
CPC ........ *G06T 11/005* (2013.01); *G01B 9/02091* (2013.01); *G01B 9/021* (2013.01); *G06T 11/006* (2013.01); *H04N 23/56* (2023.01)

(58) Field of Classification Search
CPC . G06T 11/005; G06T 11/006; G01B 9/02091; G01B 9/021; G01B 9/02007;
(Continued)

(56) References Cited

U.S. PATENT DOCUMENTS

| 2004/0042056 A1 | 3/2004 | Price et al. |
| 2008/0259345 A1 | 10/2008 | Fukutake |

(Continued)

FOREIGN PATENT DOCUMENTS

| JP | 2005-537518 A | 12/2005 |
| JP | 2014010411 A | * 1/2014 |

(Continued)

OTHER PUBLICATIONS

Cremer et al, Super-resolution microscopy approaches to nuclear nanostructure imaging, 2017, Methods 123 2017): 11-32. (Year: 2017).*

(Continued)

*Primary Examiner* — Kathleen M Broughton
(74) *Attorney, Agent, or Firm* — Sughrue Mion, PLLC

(57) ABSTRACT

A control device includes a processor. The processor acquires positional information indicating a position of an observation target. The processor sets, from among a plurality of irradiation positions, a required irradiation position, which is an irradiation position corresponding to the position of the observation target indicated by the positional information and is an irradiation position required for obtaining a plurality of the interference fringe images that are sources of a super-resolution interference fringe image having a resolution exceeding a resolution of an imaging element. The processor causes a light source to emit an illumination light from the required irradiation position by controlling an operation of the light source, and causes the imaging element to outputs the interference fringe image at each required irradiation position.

11 Claims, 33 Drawing Sheets

(51) Int. Cl.
*G06T 11/00* (2006.01)
*H04N 23/56* (2023.01)

(58) Field of Classification Search
CPC ... G01B 9/02047; H04N 23/56; C12M 41/46;
G01N 15/0227; G01N 15/1425; G01N
15/1433; G01N 15/1429; G01N 15/1434;
G01N 2015/1493; G01N 2015/144; G01N
2015/1006; G01N 2015/1454; G03H
2001/005; G03H 2001/0212; G03H
2210/30; G03H 2227/03; G03H 1/0866;
G03H 1/265; G03H 1/0443; G03H
2001/0447; G03H 2001/046; G03H
2222/34; G03H 2240/56; G02B 21/0008;
G02B 21/06
See application file for complete search history.

(56) References Cited

U.S. PATENT DOCUMENTS

| | | | |
|---|---|---|---|
| 2013/0280752 A1 | 10/2013 | Ozcan et al. | |
| 2014/0146376 A1* | 5/2014 | Kleppe | G02B 21/0072 |
| | | | 359/385 |
| 2014/0209806 A1 | 7/2014 | Nishino et al. | |
| 2014/0374575 A1* | 12/2014 | Takesue | G01B 9/02002 |
| | | | 250/208.5 |
| 2018/0052425 A1 | 2/2018 | Ozcan et al. | |
| 2019/0137754 A1* | 5/2019 | Sase | G02B 21/367 |
| 2019/0146201 A1* | 5/2019 | Ouchi | G02B 21/0076 |
| | | | 359/388 |

FOREIGN PATENT DOCUMENTS

| | | |
|---|---|---|
| JP | 2014-507645 A | 3/2014 |
| WO | 2008/123408 A1 | 10/2008 |
| WO | 2013/046875 A1 | 4/2013 |
| WO | WO-2016151665 A1 * | 9/2016 |

OTHER PUBLICATIONS

Luo et al, Pixel super-resolution using wavelength scanning, 2016, Light: Science and Applications 5, e16060, pp. 1-11. (Year: 2016).*
Extended European Search Report dated Jan. 3, 2023 in Application No. 20898699.2.
Bishara et al., "Lensfree on-chip microscopy over a wide field-of-view using pixel super-resolution", Optics Express, May 24, 2010, vol. 18, No. 11, pp. 11181-11191 (11 total pages).
International Search Report dated Dec. 28, 2020 in International Application No. PCT/JP2020/038538.
International Preliminary Report on Patentability dated May 17, 2022 in International Application No. PCT/JP2020/038538.
Written Opinion of the International Searching Authority dated Dec. 28, 2020 in International Application No. PCT/JP2020/038538.

* cited by examiner

FIG. 14

| REGION IN WHICH CENTER POINT OF INTERFERENCE FRINGE IS POSITIONED | REQUIRED IRRADIATION POSITION |
|---|---|
| R11 | IP14,IP15,IP24,IP25 |
| R12 | IP13,IP14,IP15,IP23,IP24,IP25 |
| ... | ... |
| R22 | IP13,IP14,IP15,IP23,IP24,IP25,IP33,IP34,IP35 |
| R23 | IP12,IP13,IP14,IP22,IP23,IP24,IP32,IP33,IP34 |
| ... | ... |
| R42 | IP33,IP34,IP35,IP43,IP44,IP45,IP53,IP54,IP55 |
| R43 | IP32,IP33,IP34,IP42,IP43,IP44,IP52,IP53,IP54 |
| ... | ... |
| R54 | IP41,IP42,IP43,IP51,IP52,IP53 |
| R55 | IP41,IP42,IP51,IP52 |

| REGION IN WHICH CENTER POINT OF INTERFERENCE FRINGE IS POSITIONED = R33 | SIZE INFORMATION = LARGE |

REQUIRED IRRADIATION POSITION = IP22,IP24,IP33,IP42,IP44

FIG. 37B

| REGION IN WHICH CENTER POINT OF INTERFERENCE FRINGE IS POSITIONED = R33 | SIZE INFORMATION = MEDIUM |

REQUIRED IRRADIATION POSITION = IP22,IP23,IP24,IP32,IP33,IP34, IP42,IP43,IP44

FIG. 37C

| REGION IN WHICH CENTER POINT OF INTERFERENCE FRINGE IS POSITIONED = R33 | SIZE INFORMATION = SMALL |

REQUIRED IRRADIATION POSITION = IP11,IP13,IP15,IP22,IP23,IP24, IP31,IP32,IP33,IP34,IP35, IP42,IP43,IP44,IP51,IP53,IP55

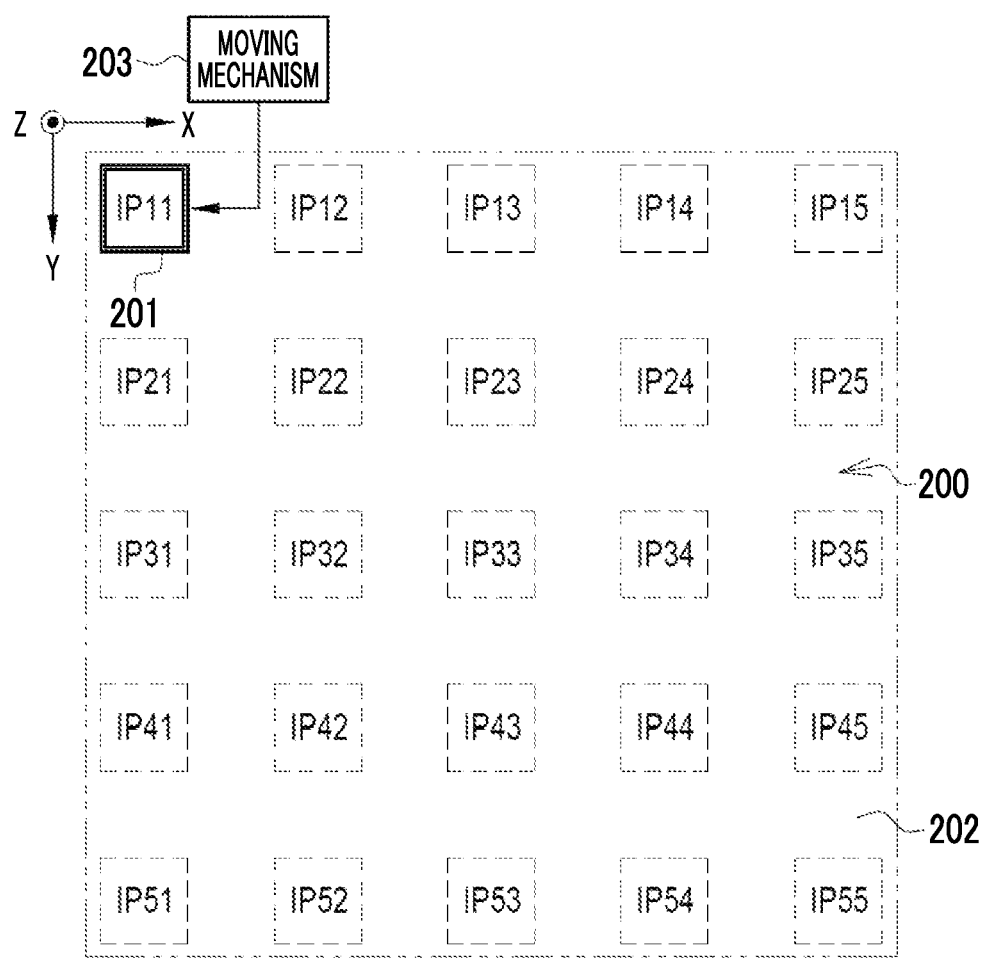

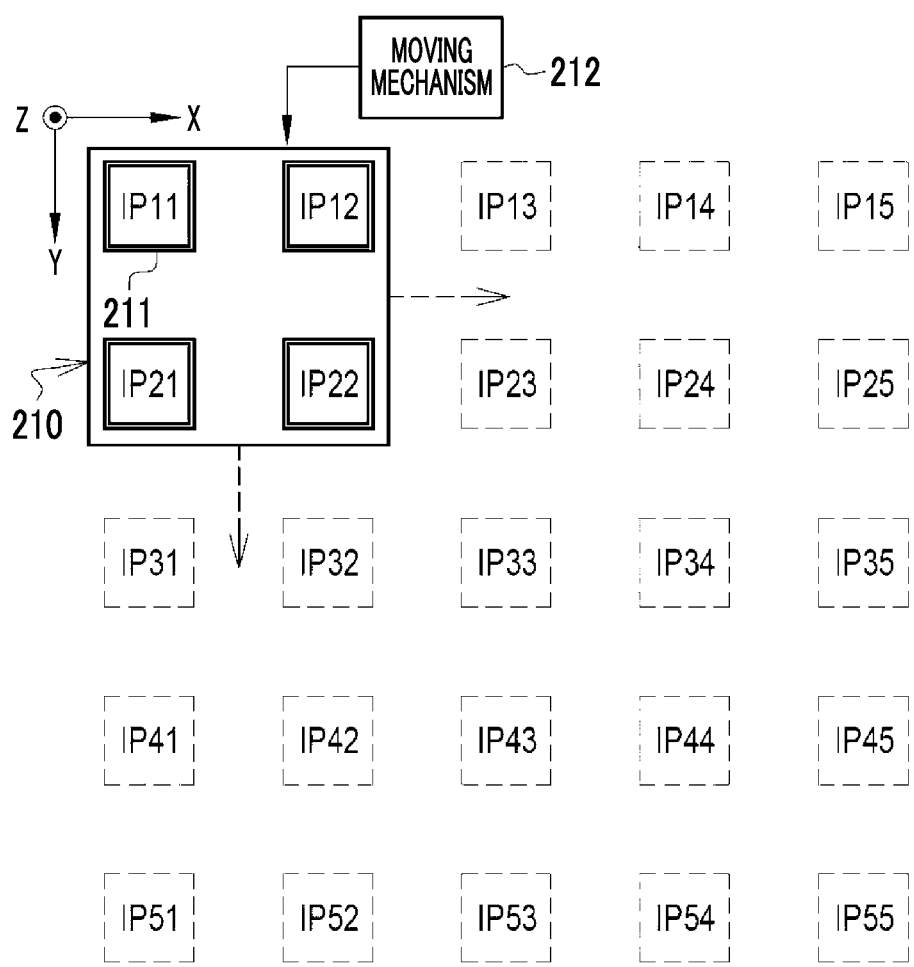

CONTROL DEVICE, OPERATION METHOD OF CONTROL DEVICE, AND OPERATION PROGRAM OF CONTROL DEVICE

CROSS-REFERENCE TO RELATED APPLICATIONS

This application is a continuation application of International Application No. PCT/JP2020/038538 filed on Oct. 12, 2020, the disclosure of which is incorporated herein by reference in its entirety. Further, this application claims priority from Japanese Patent Application No. 2019-223581 filed on Dec. 11, 2019, the disclosure of which is incorporated herein by reference in its entirety.

BACKGROUND

1. Technical Field

The technology of the present disclosure relates to a control device, an operation method of a control device, and an operation program of a control device.

2. Description of the Related Art

In digital holography, a light source irradiates an observation target with illumination light. Moreover, an interference fringe image is output from an imaging element by imaging, but the imaging element, an interference fringe between diffracted light which is illumination light diffracted by the observation target and reference light which is illumination light that does not pass through the observation target. The interference fringe image includes information on the observation target in a thickness direction along an irradiation direction of the illumination light. Therefore, by performing appropriate operation processing on the interference fringe image, it is possible to obtain a reconstructed image representing any tomographic plane of the observation target.

JP2014-507645A discloses the technology of generating a super-resolution interference fringe image having a resolution exceeding a resolution of an imaging element and generating a reconstructed image from the super-resolution interference fringe image. Specifically, in JP2014-507645A, illumination light is emitted from a plurality of irradiation positions having different irradiation angles, and an interference fringe image is output for each of the plurality of irradiation positions. Moreover, the super-resolution interference fringe images are generated based on the plurality of interference fringe images at the irradiation positions.

SUMMARY

In JP2014-507645A, the illumination light is emitted from all of the plurality of irradiation positions, and the interference fringe image is output each time of the irradiation. However, depending on the position of the observation target, the interference fringe image, which has almost no contribution to a super-resolution and can be omitted, may be present in the plurality of interference fringe images corresponding to the plurality of irradiation positions. In this case, processing of capturing the interference fringe image having almost no contribution to the super-resolution is wasted.

The technology of the present disclosure is to provide a control device, an operation method of a control device, and an operation program of a control device in which a super-resolution interference fringe image having a resolution exceeding a resolution of an imaging element can be obtained without wasteful labor.

In order to achieve the above object, the present disclosure relates to a control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the control device comprising an acquisition unit that acquires positional information indicating a position of the observation target, a setting unit that sets, from among the plurality of irradiation positions, a required irradiation position, which is an irradiation position corresponding to the position of the observation target indicated by the positional information and is an irradiation position required for obtaining a plurality of the interference fringe images that are sources of a super-resolution interference fringe image having a resolution exceeding a resolution of the imaging element, a light source control unit that emits the illumination light from the required irradiation position by controlling an operation of the light source, and an imaging control unit that outputs the interference fringe image from the imaging element at each required irradiation position.

It is preferable that the light source have a configuration in which a plurality of light emission units of the illumination light are arranged at the plurality of irradiation positions, and the light source control unit emit the illumination light from the light emission unit corresponding to the required irradiation position.

It is preferable that the light source include at least one light emission unit of the illumination light and a moving mechanism of the light emission unit, and the light source control unit emit the illumination light from the light emission unit while moving the light emission unit to the required irradiation position by the moving mechanism.

It is preferable that the acquisition unit acquire the positional information by detecting the position of the observation target from a standard interference fringe image, which is the interference fringe image obtained by emitting the illumination light from one preset standard irradiation position among the plurality of irradiation positions, or a standard reconstructed image, which is a reconstructed image representing any tomographic plane of the observation target and is a reconstructed image generated based on the standard interference fringe image.

It is preferable that the control device further comprise a display control unit that performs a control of displaying a display screen of a standard interference fringe image, which is the interference fringe image obtained by emitting the illumination light from one preset standard irradiation position among the plurality of irradiation positions, or a display screen of a standard reconstructed image, which is a reconstructed image representing any tomographic plane of the observation target and is a reconstructed image generated based on the standard interference fringe image, in which the acquisition unit acquires the positional information by receiving designation of the position of the observation target on the display screen.

It is preferable that the acquisition unit acquire size information indicating a size of the observation target, in addition to the positional information, and the setting unit change the number of the required irradiation positions in accordance with the size information.

It is preferable that, in a case in which a plurality of the observation targets are present and the required irradiation positions of the plurality of observation targets overlap, the light source control unit emit the illumination light only once from overlapping required irradiation positions.

It is preferable that the observation target be a cell in culture.

It is preferable that the illumination light be coherent light.

The present disclosure relates to an operation method of a control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the operation method comprising an acquisition step of acquiring positional information indicating a position of the observation target, a setting step of setting, from among the plurality of irradiation positions, a required irradiation position, which is an irradiation position corresponding to the position of the observation target indicated by the positional information and is an irradiation position required for obtaining a plurality of the interference fringe images that are sources of a super-resolution interference fringe image having a resolution exceeding a resolution of the imaging element, a light source control step of emitting the illumination light from the required irradiation position by controlling an operation of the light source, and an imaging control step of outputting the interference fringe image from the imaging element at each required irradiation position.

The present disclosure relates to an operation program of a control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the operation program causing a computer to function as an acquisition unit that acquires positional information indicating a position of the observation target, a setting unit that sets, from among the plurality of irradiation positions, a required irradiation position, which is an irradiation position corresponding to the position of the observation target indicated by the positional information and is an irradiation position required for obtaining a plurality of the interference fringe images that are sources of a super-resolution interference fringe image having a resolution exceeding a resolution of the imaging element, a light source control unit that emits the illumination light from the required irradiation position by controlling an operation of the light source, and an imaging control unit that outputs the interference fringe image from the imaging element at each required irradiation position.

According to the technology of the present disclosure, it is possible to provide the control device, the operation method of the control device, and the operation program of the control device in which the super-resolution interference fringe image having the resolution exceeding the resolution of the imaging element can be obtained without wasteful labor.

BRIEF DESCRIPTION OF THE DRAWINGS

Exemplary embodiments according to the technique of the present disclosure will be described in detail based on the following figures, wherein:

FIG. 5A shows the formation of a bright portion of the interference fringe, and FIG. 5B shows the formation of a dark portion of the interference fringe;

FIG. 8A shows a case in which coherent light is emitted from certain light emission unit, and FIG. 8B shows a case in which the coherent light is emitted from the light emission unit adjacent to the light emission unit of FIG. 8A in an X direction;

FIG. 14 is a view showing a required irradiation position table;

FIGS. 37A to 37C are views showing a specific example of the required irradiation position according to the third embodiment, FIG. 37A shows a case in which the size of the cell is large, FIG. 37B shows a case in which the size of the cell is medium, and FIG. 37C shows a case in which the size of the cell is small;

FIG. 38 is a plan view showing a light source according to a fourth embodiment;

FIG. 39 is a view showing another example of the light source; and

DETAILED DESCRIPTION

First Embodiment

Figure 1:
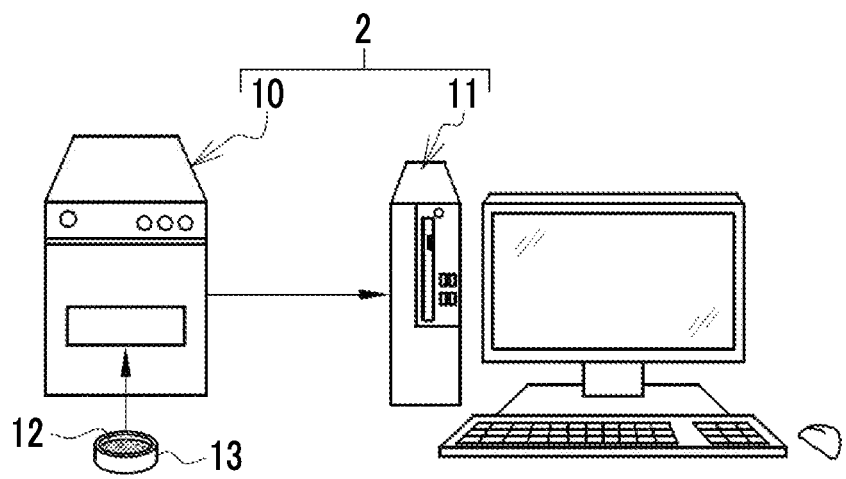
FIG. 1 is a view showing a digital holography system.

In FIG. 1, a digital holography system 2 is composed of an imaging apparatus 10 and an information processing apparatus 11. The imaging apparatus 10 and the information processing apparatus 11 are electrically connected to each other, and data can be exchanged with each other. A culture container 13 for a cell 12 is introduced into the imaging apparatus 10. The cell 12 is an example of an "observation target" according to the technology of the present disclosure. The information processing apparatus 11 is, for example, a desktop-type personal computer.

Figure 2:
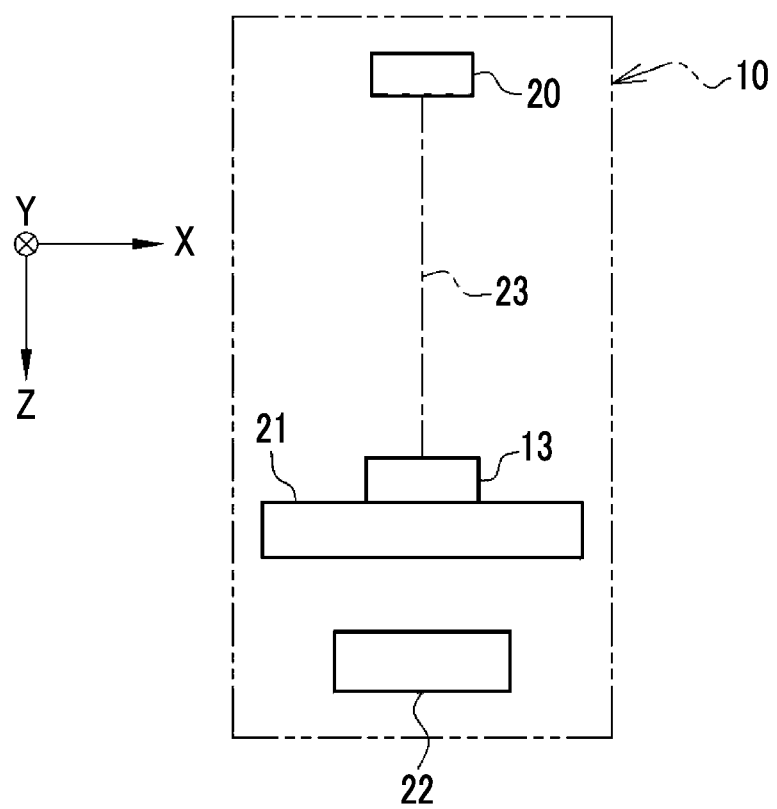
FIG. 2 is a view showing an imaging apparatus.
Figure 3:
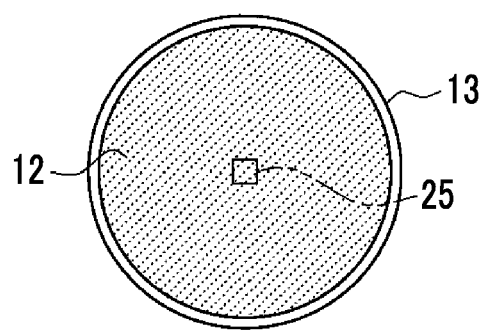
FIG. 3 is a view showing an observation region.

In FIG. 2, the imaging apparatus 10 comprises a light source 20, a stage 21, and an imaging element 22. The light source 20 emits coherent light 23 to the culture container 13 placed on the stage 21. The coherent light 23 is incident on the cell 12 and the culture container 13. More specifically, as shown in FIG. 3, the entire region of an observation region 25, which is a partial region in the vicinity of the center of the culture container 13, is irradiated with the coherent light 23. The observation region 25 has a size of 1 mm×1 mm, for example. The coherent light 23 is an example of "illumination light" according to the technology of the present disclosure. It should be noted that a Z direction is an irradiation direction of the coherent light 23. An X direction and a Y direction are directions orthogonal to the Z direction and parallel to an imaging surface 32 (see FIG. 4) of the imaging element 22. In addition, the X direction and the Y direction are directions orthogonal to each other and are directions along an arrangement direction of pixels 45 (see FIG. 8) of the imaging element 22.

Figure 4:
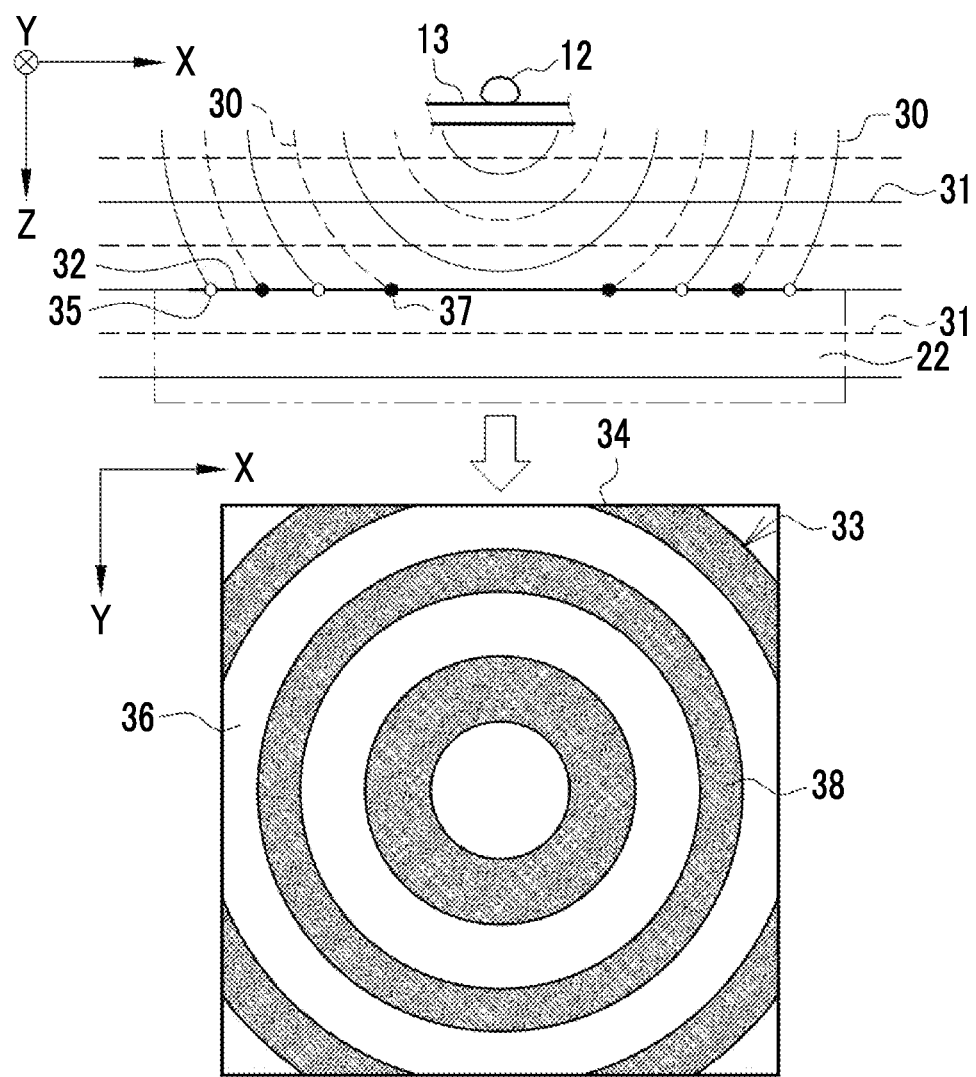
FIG. 4 is a view showing a state of diffracted light and transmitted light in a vicinity of an imaging surface of an imaging element, and an interference fringe image.

As shown in FIG. 4, the coherent light 23 incident on the cell 12 and the culture container 13 is divided into diffracted light 30 diffracted by the cell 12 and the culture container 13 and transmitted light 31 transmitted without passing through the cell 12 and the culture container 13. The diffracted light 30 and the transmitted light 31 interfere with each other on the imaging surface 32 of the imaging element 22 to generate an interference fringe 33. The imaging element 22 images the interference fringe 33 and outputs an interference fringe image 34. The transmitted light 31 is an example of "reference light" according to the technology of the present disclosure.

Figure 5A:
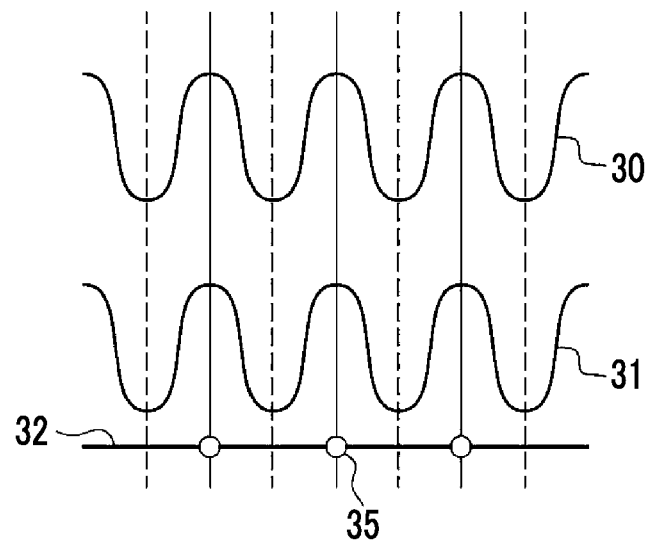
FIGS. 5A and 5B are views for describing the formation of an interference fringe.
Figure 5B:
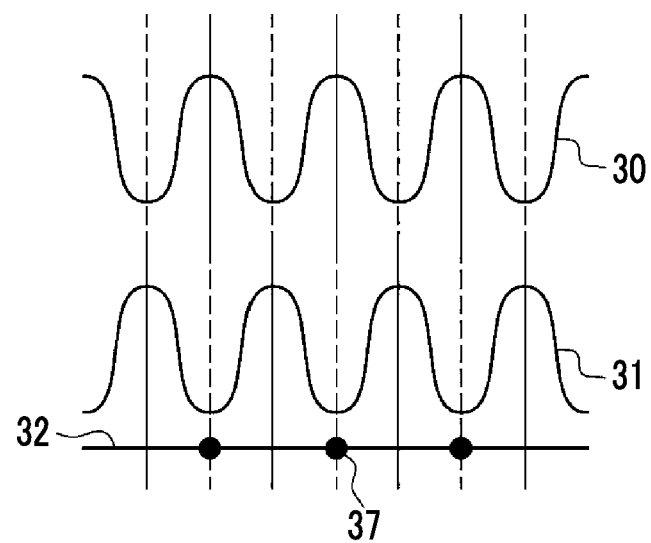

As shown in FIG. 5, among lines representing the diffracted light 30 and the transmitted light 31, a solid line indicates a wave surface having the maximum amplitude of the diffracted light 30 and the transmitted light 31. On the other hand, a broken line indicates a wave surface having the minimum amplitude of the diffracted light 30 and the transmitted light 31. A white spot 35 shown on the imaging surface 32 is a portion in which the wave surfaces of the diffracted light 30 and the transmitted light 31 are aligned and strengthened (see FIG. 5A). This portion of the white spot 35 appears as a bright portion 36 in the interference fringe 33. On the other hand, a black spot 37 shown on the imaging surface 32 is a portion in which the wave surfaces of the diffracted light 30 and the transmitted light 31 deviate by half a wavelength and are weakened (see FIG. 5B). This portion of the black spot 37 appears as a dark portion 38 in the interference fringe 33.

Figure 6:
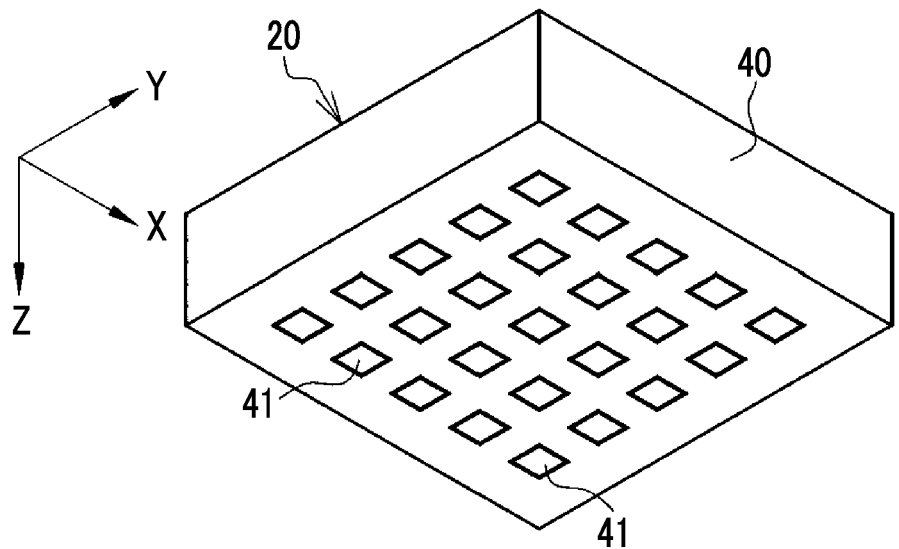
FIG. 6 is a perspective view showing a light source.

As shown in FIG. 6, the light source 20 has a rectangular parallelepiped housing 40. On a surface of the housing 40 facing the stage 21, 5×5=25 light emission units 41 are arranged at equal intervals in the X direction and the Y direction. The light emission unit 41 individually emits the coherent light 23. Examples of the light source 20 having such a configuration in which a plurality of light emission units 41 are arranged include a vertical cavity surface emitting laser (VCSEL) array element. It should be noted that the light emission unit 41 has a several μm-order size.

Figure 7:
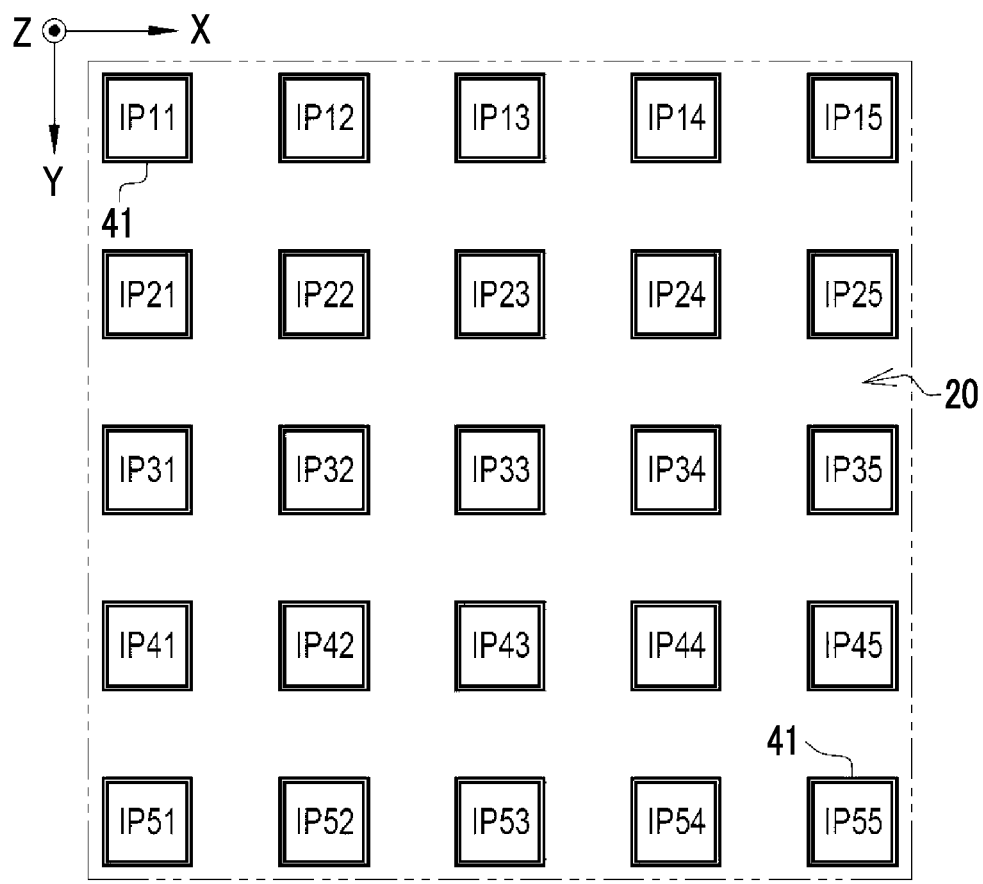
FIG. 7 is a view showing an installation position and an irradiation position of a light emission unit.

As shown in FIG. 7, installation positions of the light emission units 41, such as IP11, IP12, . . . , IP54, and IP55, are a plurality of irradiation positions of the coherent light 23 having different irradiation angles. By using the light source 20 having such a configuration in which the plurality of light emission units 41 are arranged at the plurality of irradiation positions IP11 to IP55, a super-resolution interference fringe image 104 (see FIG. 22 and the like) having a resolution exceeding a resolution of the imaging element 22 can be generated. It should be noted that "different irradiation angles" means that incidence angles of the coherent light 23 on the imaging surface 32 of the imaging element 22 are different. In addition, FIG. 7 is a view of the light source 20 as viewed from a side of the imaging element 22.

Figure 8A:
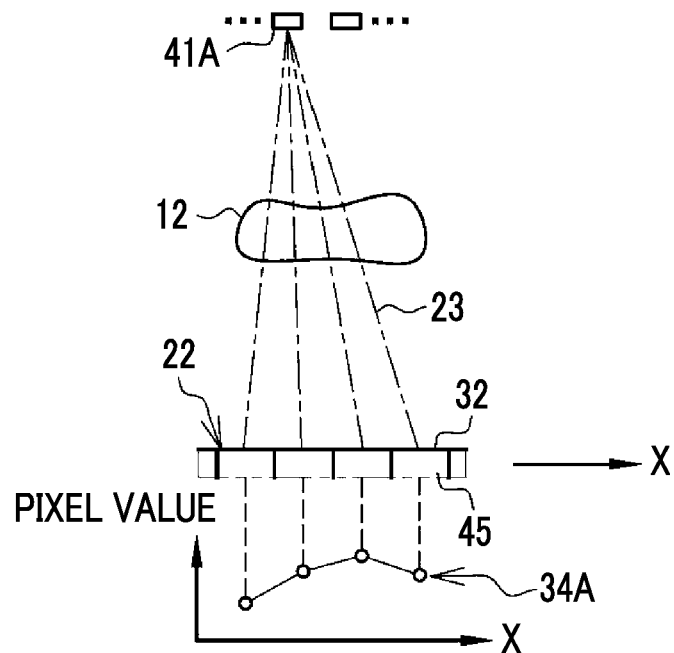
FIGS. 8A and 8B are views conceptually showing the generation principle of a super-resolution interference fringe image.
Figure 8B:
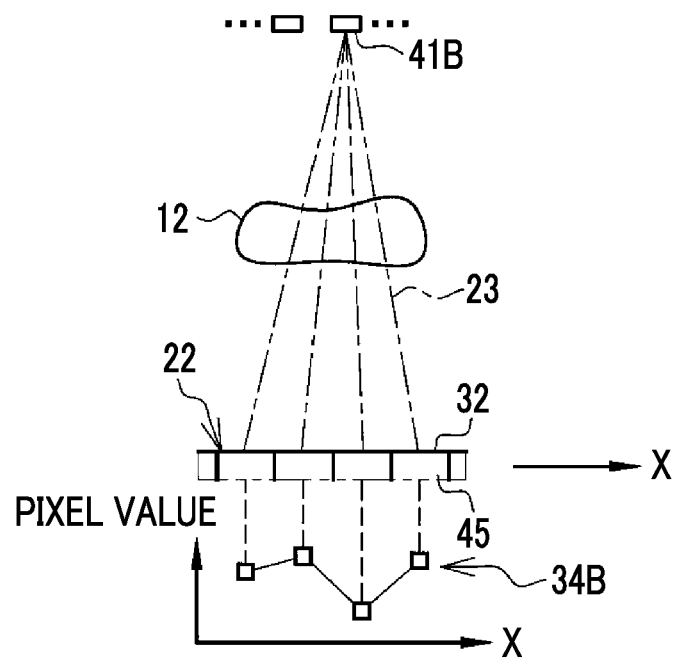
Figure 9:
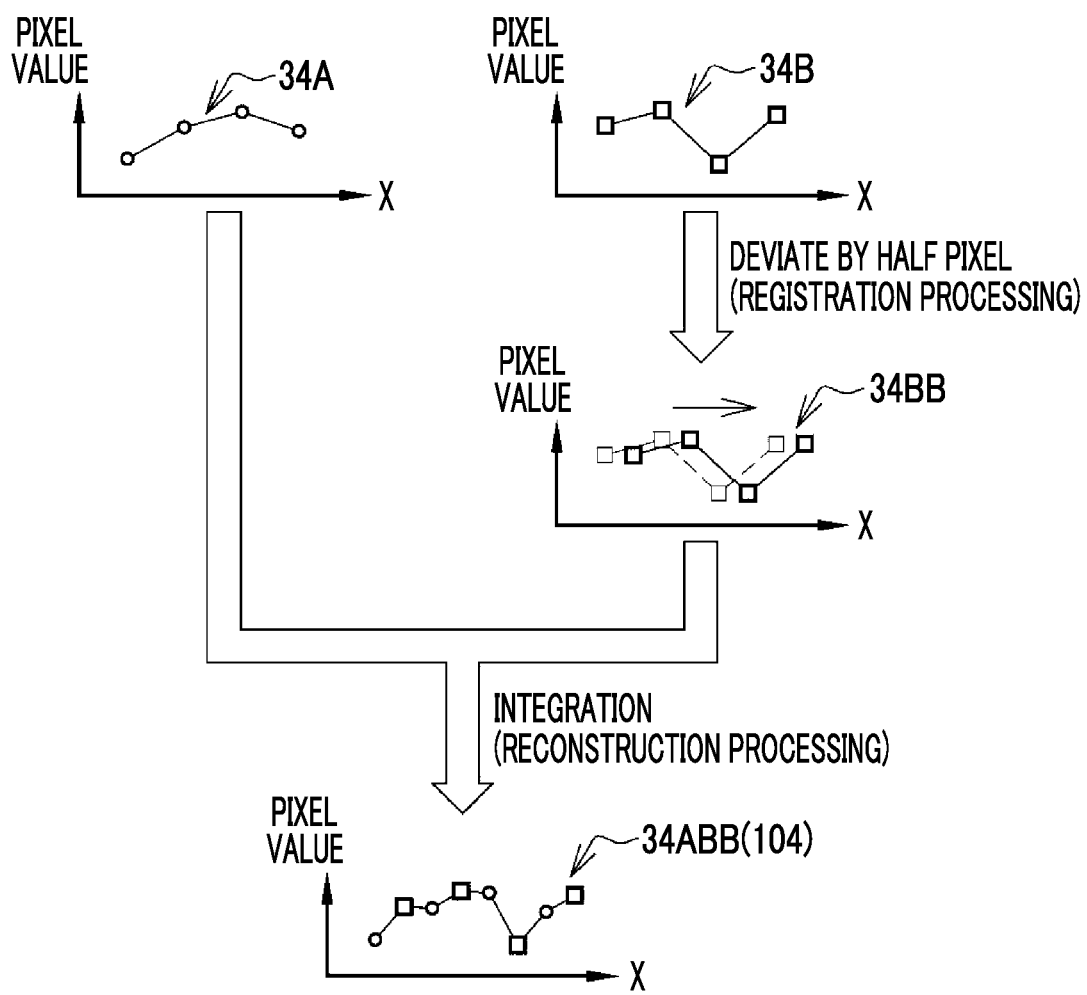
FIG. 9 is a view conceptually showing the generation principle of the super-resolution interference fringe image.

FIGS. 8A and 8B, and 9 are views conceptually showing the generation principle of the super-resolution interference fringe image 104. First, in FIGS. 8A to 8B, FIG. 8A shows a case in which the coherent light 23 is emitted from certain light emission unit 41A, and FIG. 8B shows a case in which the coherent light 23 is emitted from a light emission unit 41B adjacent to the light emission unit 41A of FIG. 8A in the X direction. The incidence angle of the coherent light 23 from the light emission unit 41A on the cell 12 is different from the incidence angle of the coherent light 23 from the light emission unit 41B on the cell 12. Therefore, pieces of information on the interference fringe 33 by the cell 12 obtained by the pixels 45 of the imaging element 22 are also different. Therefore, interference fringe images 34A and 34B having different pixel values are obtained in a case of FIG. 8A and a case of FIG. 8B, respectively. A circle mark represents a pixel value of the interference fringe image 34A, and a square mark represents a pixel value of the interference fringe image 34B. It should be noted that the pixel 45 of the imaging element 22 has a size of 2 μm×2 μm, for example.

It is assumed that a sampling point of the cell 12 deviates by half of the pixel 45, that is, by half a pixel between a case of FIG. 8A and a case of FIG. 8B. In this case, as shown in FIG. 9, for example, the interference fringe image 34B obtained in a case of FIG. 8B deviate by half a pixel with the interference fringe image 34A obtained in a case of FIG. 8A as a standard to obtain an interference fringe image 34BB. Then, the interference fringe image 34A obtained in a case of FIG. 8A and the interference fringe image 34BB are integrated into an interference fringe image 34ABB. The interference fringe image 34ABB is an image having twice the number of pixels as the interference fringe images 34A and 34B. That is, the interference fringe image 34ABB is none other than the super-resolution interference fringe image 104 having the resolution exceeding the resolution of the imaging element 22. It should be noted that the processing of causing the interference fringe image 34B to deviate by half a pixel to obtain the interference fringe image 34BB is called registration processing. In addition, the processing of integrating the interference fringe image 34A and the interference fringe image 34BB is called reconstruction processing.

In FIGS. 8A and 8B, and 9, the description is made in one dimension only in the X direction, but the basic idea of the generation principle of the super-resolution interference fringe image 104 is the same even in the two dimensions in which the Y direction is added. For example, a case is considered in which the coherent light 23 is emitted from 2×2=4 light emission units 41 adjacent to each other in the X direction and the Y direction, and the interference fringe image 34 is output from the imaging element 22 each time of the irradiation. In this case, it is assumed that the sampling point of the cell 12 deviates by half a pixel as described above, the super-resolution interference fringe image 104 having 2×2=4 times the number of pixels as the interference fringe image 34 output from the imaging element 22 is obtained.

Figure 10:
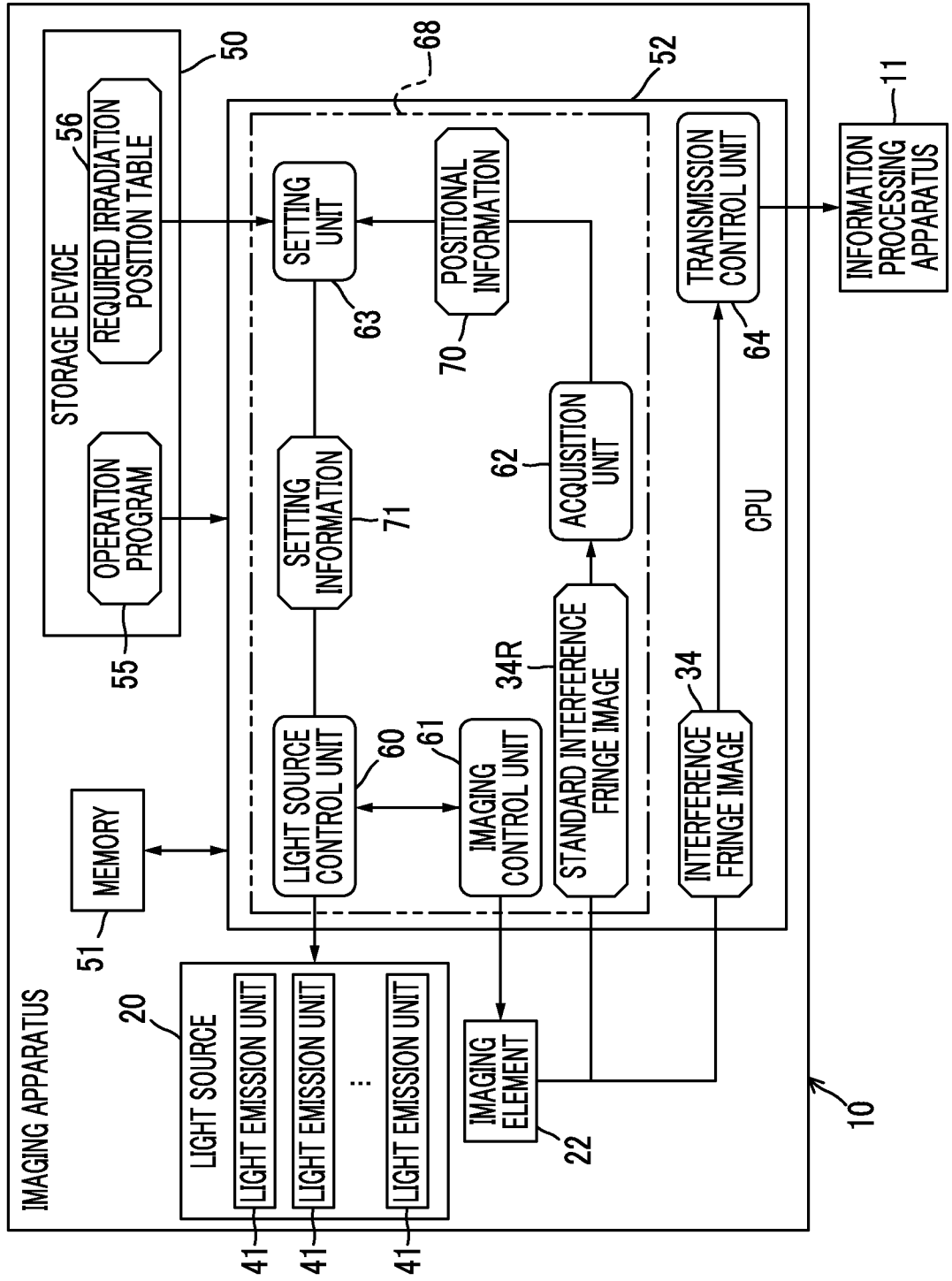
FIG. 10 is a block diagram showing a processing unit of a CPU of the imaging apparatus.

In FIG. 10, the imaging apparatus 10 comprises a storage device 50, a memory 51, and a central processing unit (CPU) 52. The storage device 50 and the memory 51 are connected to the CPU 52. The storage device 50, the memory 51, and the CPU 52 are examples of a "computer" according to the technology of the present disclosure.

The storage device 50 is a hard disk drive or a solid state drive. The memory 51 is a work memory in which the CPU 52 executes processing. The CPU 52 loads the program stored in the storage device 50 to the memory 51 and executes the processing in accordance with the program to comprehensively control the units of the computer.

An operation program 55 is stored in the storage device 50. The operation program 55 is an application program for causing the computer composed of the storage device 50, the memory 51, and the CPU 52 function as a control device. That is, the operation program 55 is an example of an "operation program of a control device" according to the technology of the present disclosure. A required irradiation position table 56 is also stored in the storage device 50.

In a case in which the operation program 55 is activated, the CPU 52 functions as a light source control unit 60, an imaging control unit 61, an acquisition unit 62, a setting unit 63, and a transmission control unit 64, in cooperation with the memory 51 and the like. Among these units, the light source control unit 60, the imaging control unit 61, the acquisition unit 62, and the setting unit 63 realize a control device 68 according to the present disclosure.

The light source control unit 60 controls an operation of the light source 20 and emits the coherent light 23 from the light emission unit 41. The imaging control unit 61 controls an operation of the imaging element 22 and outputs the interference fringe image 34 from the imaging element 22. The light source control unit 60 and the imaging control unit 61 synchronize an irradiation timing of the coherent light 23 from the light emission unit 41 with an imaging timing of the interference fringe image 34 by the imaging element 22.

The acquisition unit 62 receives a standard interference fringe image 34R from the imaging element 22. The acquisition unit 62 detects a position of the cell 12 from the standard interference fringe image 34R. As a result, the acquisition unit 62 acquires positional information 70 indicating the position of the cell 12. The acquisition unit 62 outputs the positional information 70 to the setting unit 63.

The setting unit 63 sets a required irradiation position, which is an irradiation position IP corresponding to the position of the cell 12 indicated by the positional information 70, from among the plurality of irradiation positions IP11 to IP55, with reference to the required irradiation position table 56. The required irradiation position is the irradiation position IP required for obtaining a plurality of interference fringe images 34 that are the sources of the super-resolution interference fringe image 104. The setting unit 63 outputs setting information 71 indicating the required irradiation position to the light source control unit 60.

The light source control unit 60 causes the light emission unit 41 to emit the coherent light 23 from the required irradiation position indicated by the setting information 71. The imaging control unit 61 causes the imaging element 22 to output the interference fringe image 34 at each required irradiation position.

The transmission control unit 64 receives the interference fringe image 34 from the imaging element 22. The transmission control unit 64 performs a control of transmitting the interference fringe image 34 to the information processing apparatus 11. It should be noted that the interference fringe image 34 may be transitorily stored in the storage device 50 and then transmitted to the information processing apparatus 11 by the transmission control unit 64.

Figure 11:
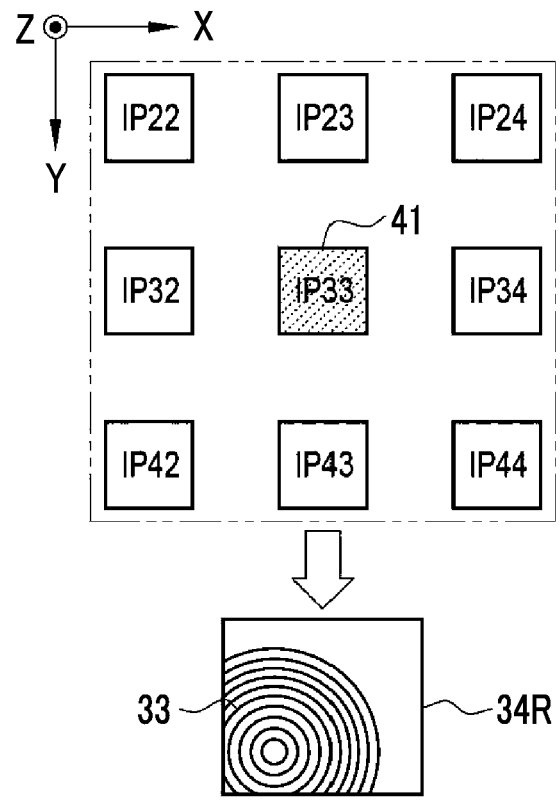
FIG. 11 is a view showing a state in which the coherent light is emitted from the light emission unit at one irradiation position positioned at the center to obtain a standard interference fringe image.

As shown in FIG. 11, the standard interference fringe image 34R is the interference fringe image 34 obtained by emitting the coherent light 23 from the light emission unit 41 at one irradiation position IP33 positioned at the center indicated by hatching among the plurality of irradiation positions IP11 to IP55. That is, the irradiation position IP33 is an example of a "standard irradiation position" according to the technology of the present disclosure.

Figure 12:
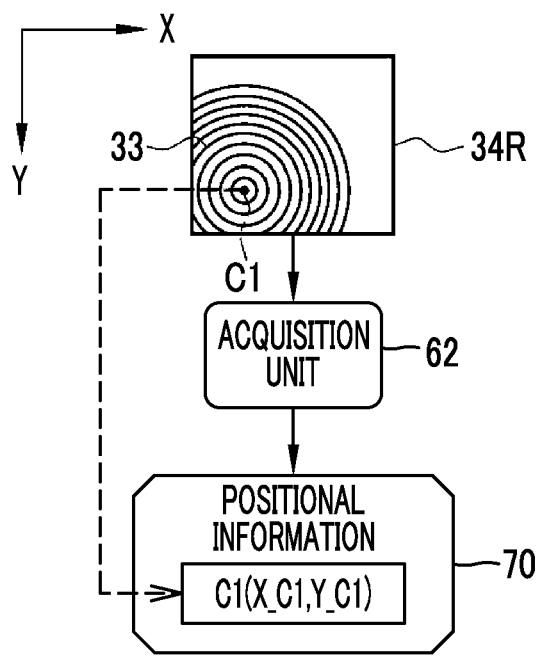
FIG. 12 is a view showing a state in which a position of a cell is detected in an acquisition unit.

As shown in FIG. 12, the acquisition unit 62 performs image analysis on the standard interference fringe image 34R and detects a position of a center point C1 of the interference fringe 33 reflected in the standard interference fringe image 34R as the position of the cell 12, for example. The acquisition unit 62 outputs a position coordinate (X_C1, Y_C1) of the center point C1 of the interference fringe 33 to the setting unit 63 as the positional information 70.

Figure 13:
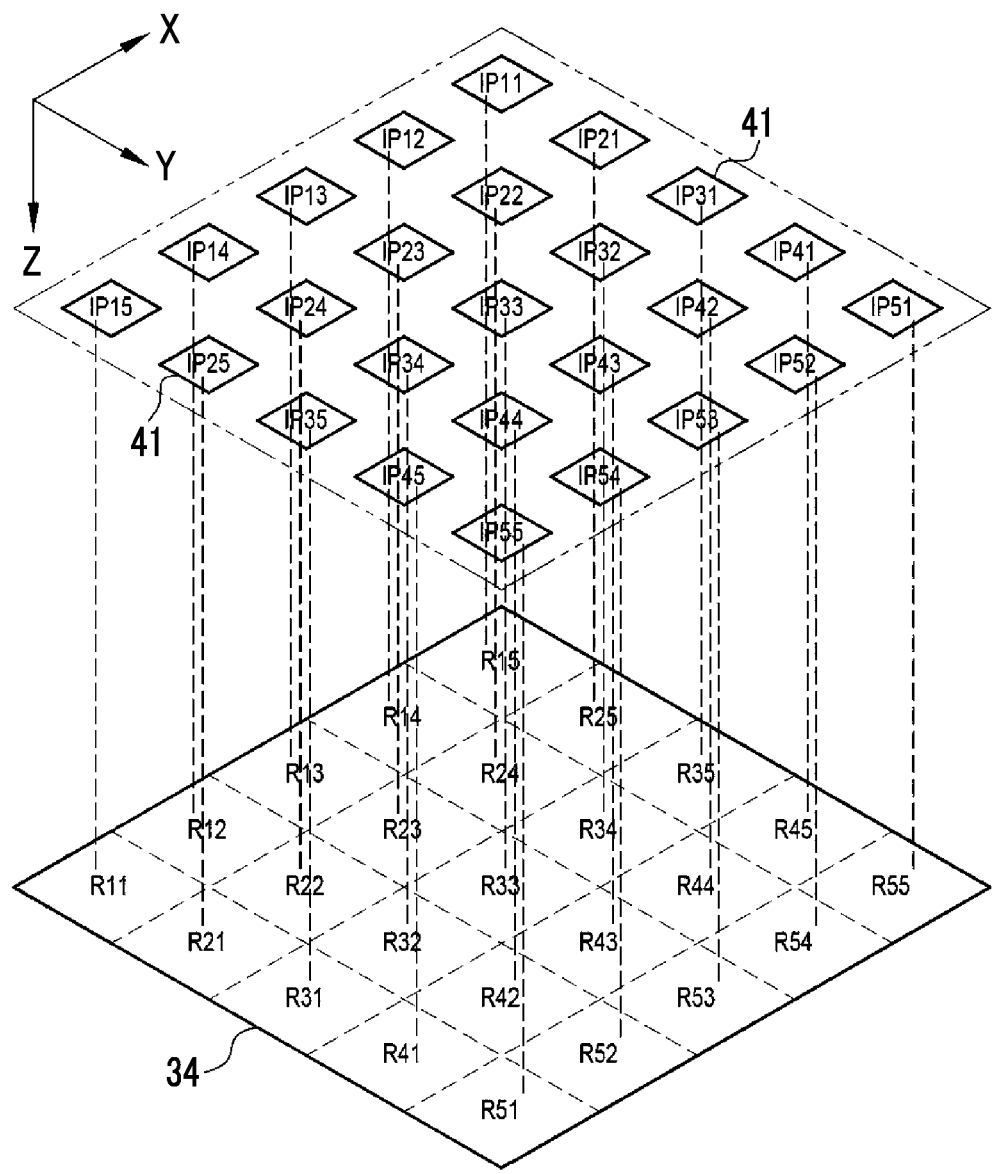
FIG. 13 is a view showing a correspondence relationship between a region of the interference fringe image and the irradiation position.

FIG. 13 is a view showing a correspondence relationship between regions R11, R12, ..., R54, and R55 obtained by dividing the interference fringe image 34 into 5×5=25 and the irradiation positions IP11 to IP55. For example, the region R11 in an upper left corner corresponds to the irradiation position IP15, and the region R15 in an upper right corner corresponds to the irradiation position IP11. In addition, the region R51 in a lower left corner corresponds to the irradiation position IP55, and the region R55 in a lower right corner corresponds to the irradiation position IP51.

In FIG. 14, in the required irradiation position table 56, the corresponding required irradiation position is registered for each of the regions R11 to R55 of the standard interference fringe image 34R. For example, in a case in which the region of the standard interference fringe image 34R in which the center point C1 of the interference fringe 33 is positioned is R11, the required irradiation positions are four of the irradiation position (hereinafter, referred to as a center point correspondence irradiation position) IP15 corresponding to the region R11, and the irradiation positions IP14, IP24, and IP25 adjacent to the center point correspondence irradiation position IP15. In a case in which the region of the standard interference fringe image 34R in which the center point C1 of the interference fringe 33 is positioned is R12, the required irradiation positions are six of the center point correspondence irradiation position IP14 corresponding to the region R12, and the irradiation positions IP13, IP15, IP23, IP24, and IP25 adjacent to the center point correspondence irradiation position IP14. In a case in which the region of the standard interference fringe image 34R in which the center point C1 of the interference fringe 33 is positioned is R42, the required irradiation positions are nine of the center point correspondence irradiation position IP44 corresponding to the region R42, and the irradiation positions IP33, IP34, IP35, IP43, IP45, IP53, IP54, and IP55 adjacent to the center point correspondence irradiation position IP44. As described above, the required irradiation position always includes the center point correspondence irradiation position corresponding to the region R of the standard interference fringe image 34R in which the center point C1 of the interference fringe 33 is positioned. Moreover, the required irradiation position is composed of the center point correspondence irradiation position and the irradiation position IP adjacent to the center point correspondence irradiation position. In addition, the number of required irradiation positions is four at the minimum and nine at the maximum.

Figure 15:
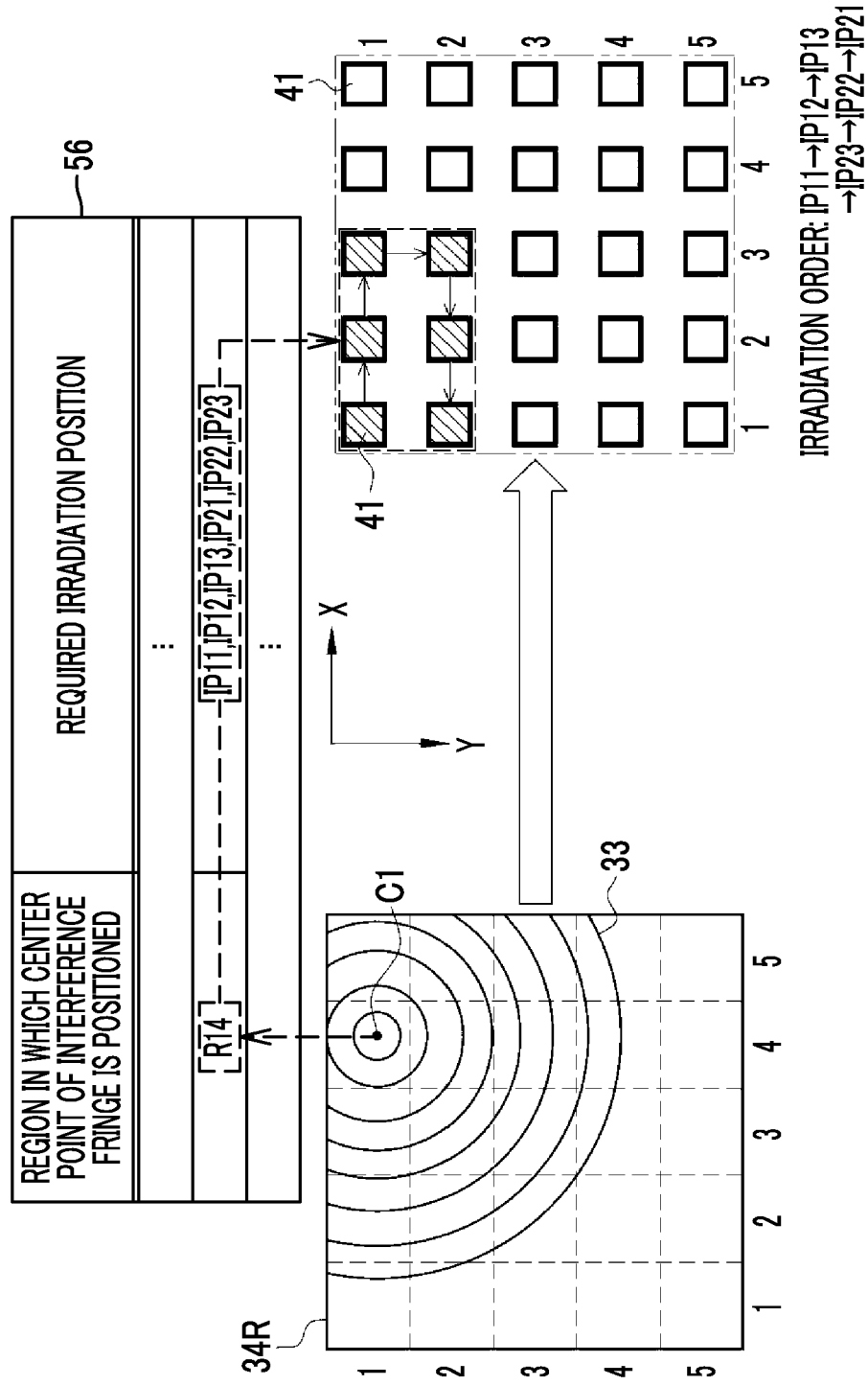
FIG. 15 is a view showing an example of a region in which a center point of the interference fringe is positioned and a required irradiation position set by a setting unit.
Figure 16:
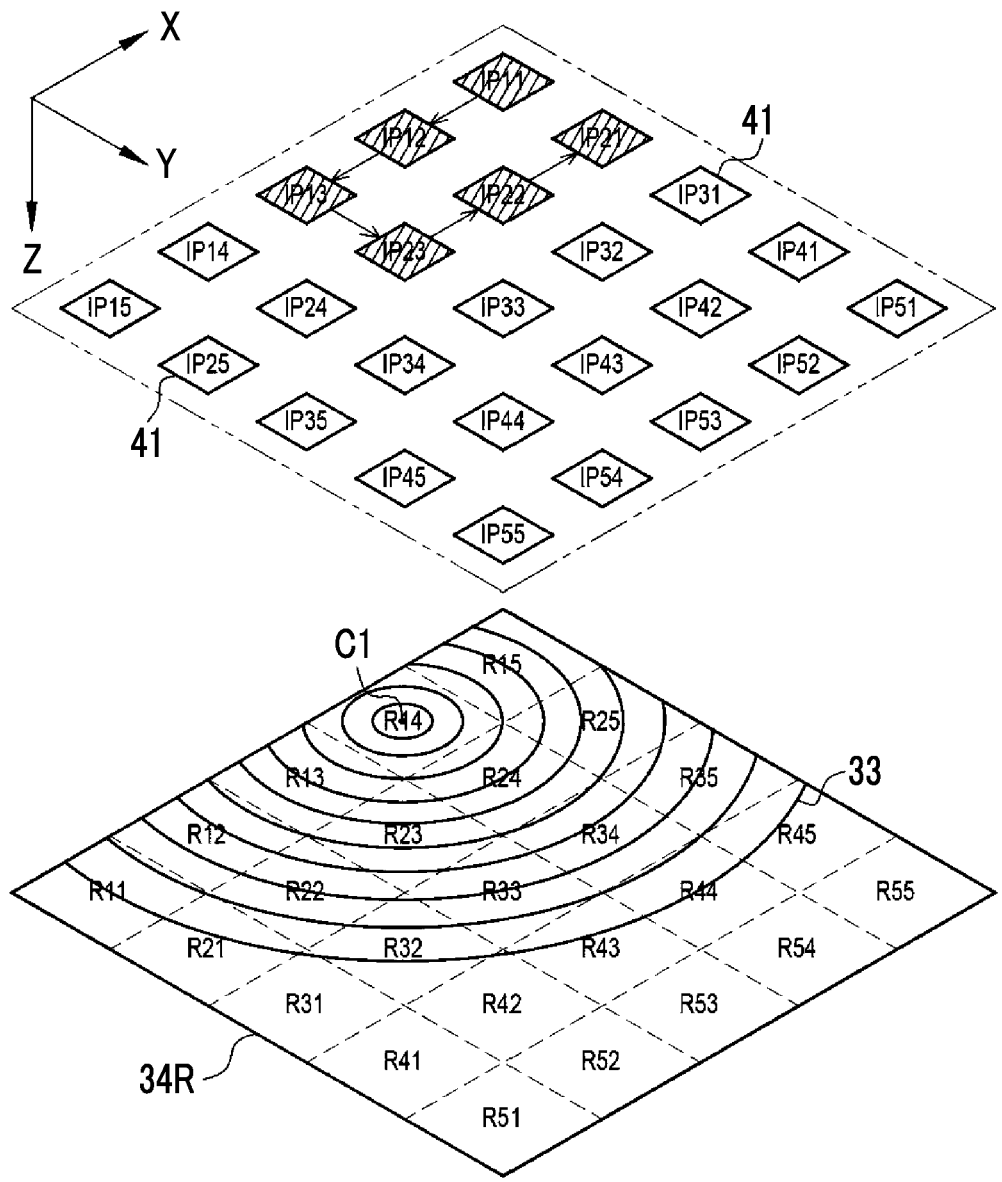
FIG. 16 is a perspective view showing an example of the region in which the center point of the interference fringe is positioned and the required irradiation position set by the setting unit.

FIGS. 15 to 20 are views showing specific examples of the required irradiation position. First, FIGS. 15 and 16 show a case in which the region of the standard interference fringe image 34R in which the center point C1 of the interference fringe 33 is positioned is R14. In this case, in accordance with the required irradiation position table 56, the required irradiation positions are the irradiation positions IP11, IP12, IP13, IP21, IP22, and IP23. The light source control unit 60 causes the light emission unit 41 to emit the coherent light 23 in the order of the irradiation positions IP11, IP12, IP13, IP23, IP22, and IP21, for example.

Figure 17:
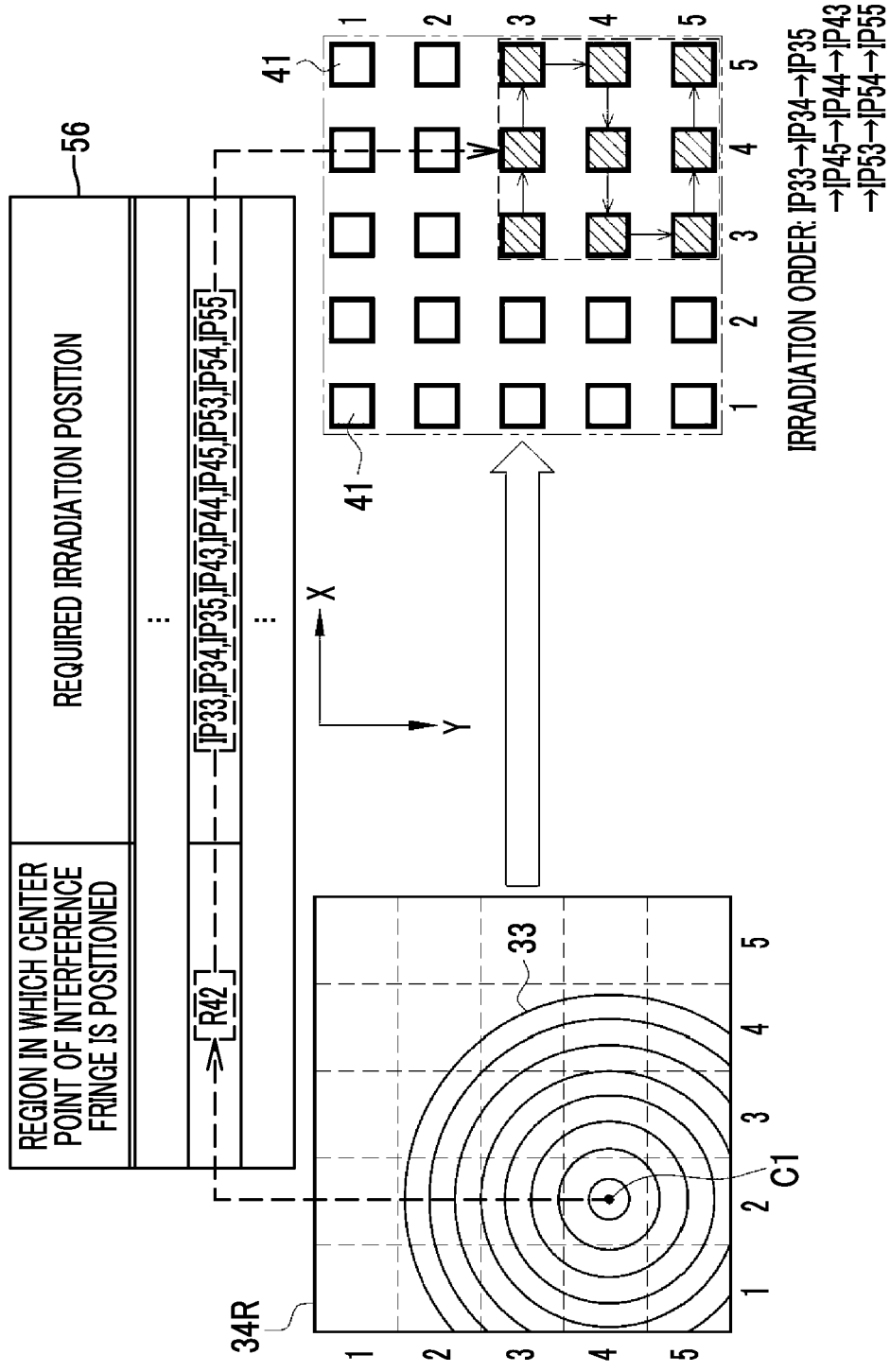
FIG. 17 is a view showing an example of the region in which the center point of the interference fringe is positioned and the required irradiation position set by the setting unit.
Figure 18:
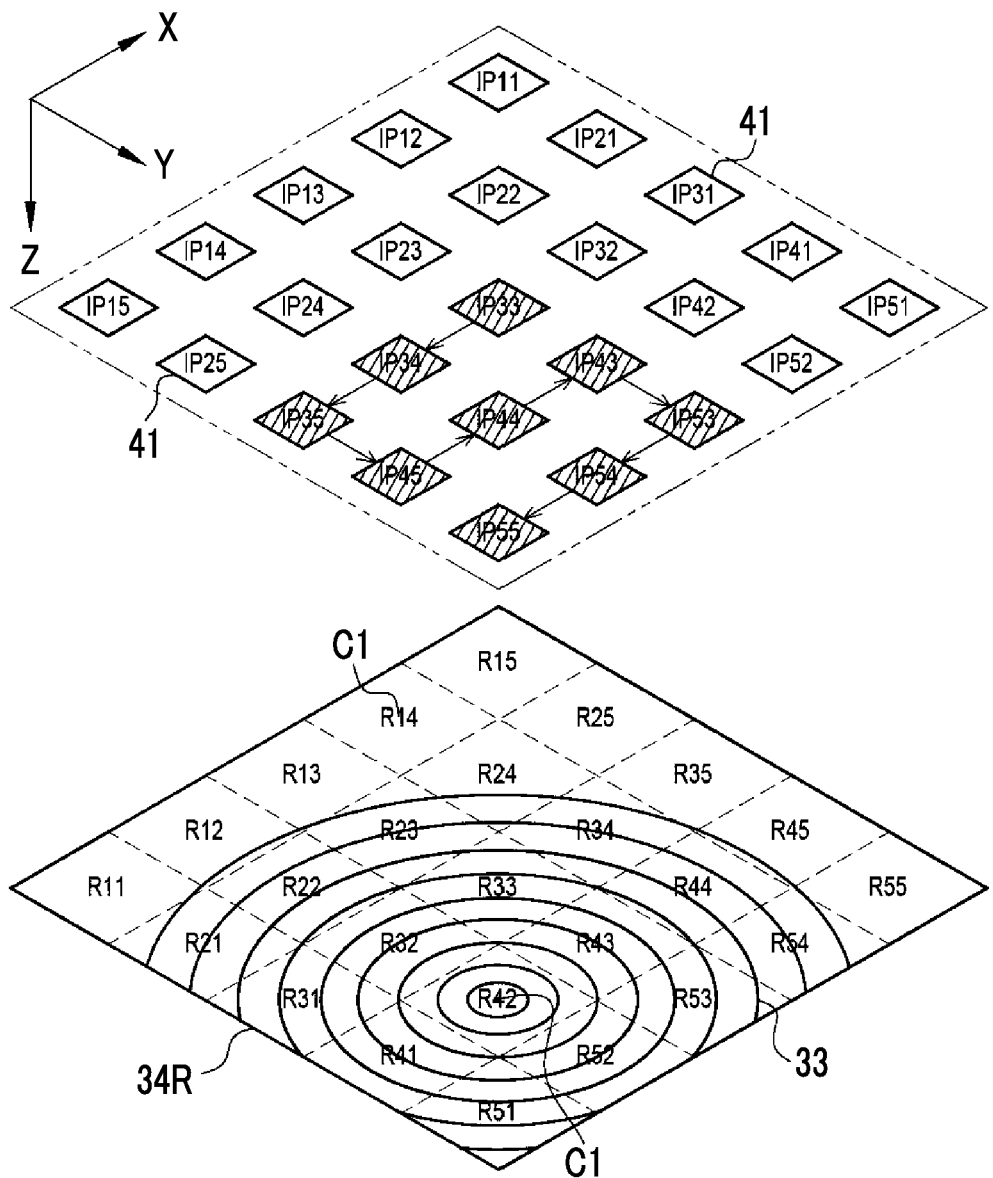
FIG. 18 is a perspective view showing an example of the region in which the center point of the interference fringe is positioned and the required irradiation position set by the setting unit.

First, FIGS. 17 and 18 show a case in which the region of the standard interference fringe image 34R in which the center point C1 of the interference fringe 33 is positioned is R42. In this case, in accordance with the required irradiation position table 56, the required irradiation positions are the irradiation positions IP33, IP34, IP35, IP43, IP44, IP45, IP53, IP54, and IP55. The light source control unit 60 causes the light emission unit 41 to emit the coherent light 23 in the order of the irradiation positions IP33, IP34, IP35, IP45, IP44, IP43, IP53, IP54, and IP55, for example.

Figure 19:
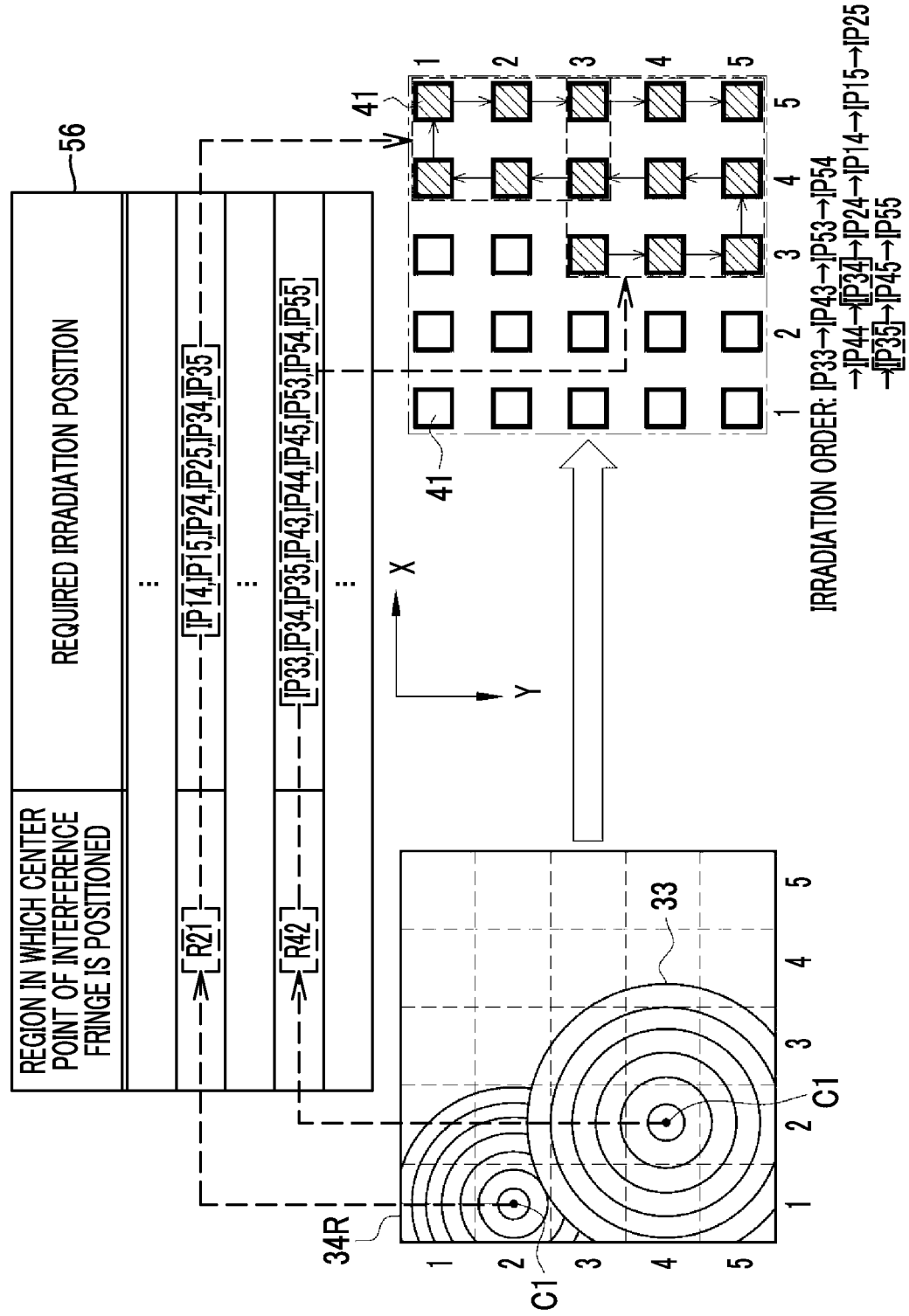
FIG. 19 is a view showing an example of the region in which the center point of the interference fringe is positioned and the required irradiation position set by the setting unit.
Figure 20:
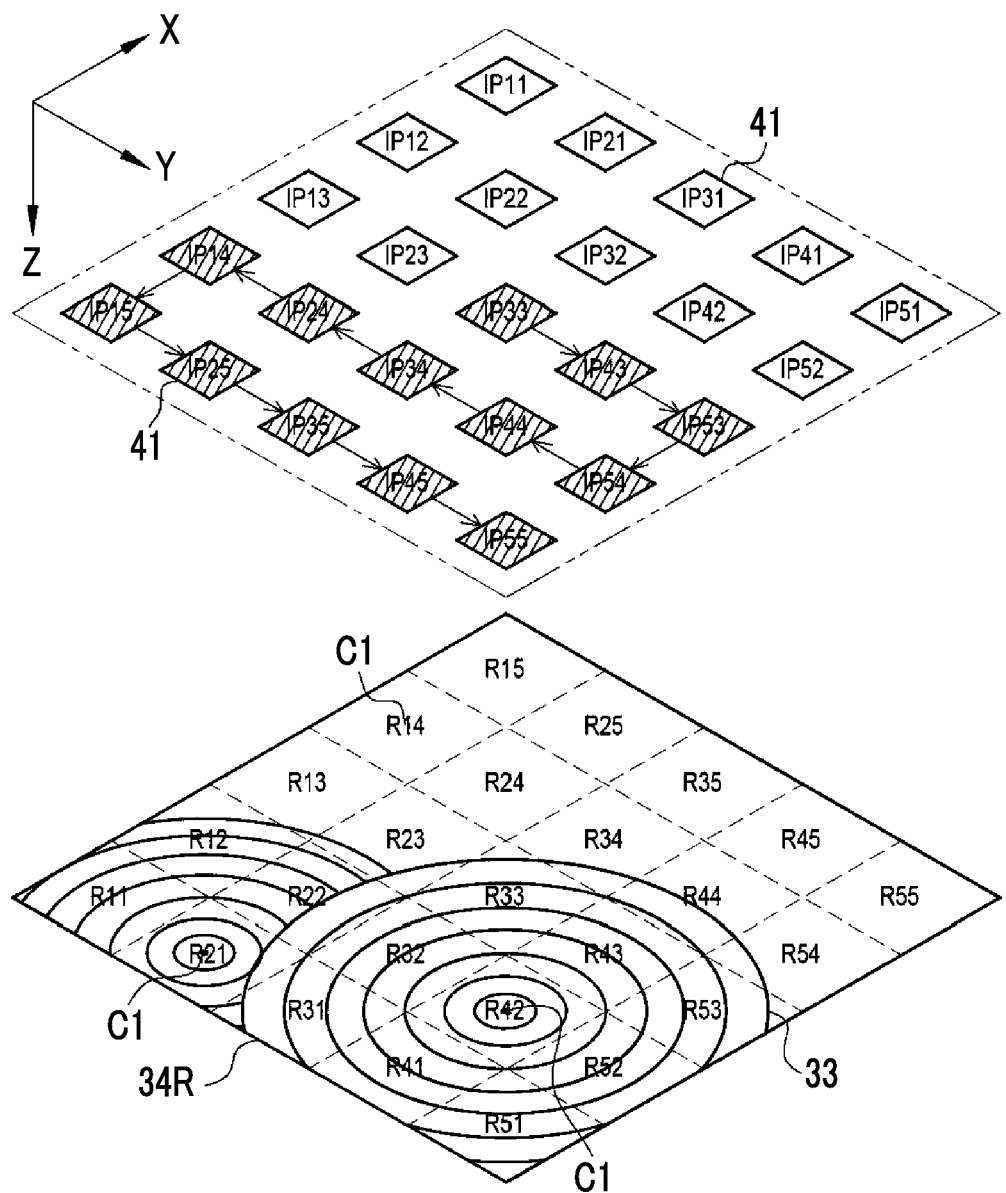
FIG. 20 is a perspective view showing an example of the region in which the center point of the interference fringe is positioned and the required irradiation position set by the setting unit.

FIGS. 15 to 18 show a case in which there is one interference fringe 33 reflected in the standard interference fringe image 34R, whereas FIGS. 19 and 20 show a case in which there are two interference fringes 33 reflected in the standard interference fringe image 34R. That is, FIGS. 19 and 20 show a case in which the regions of the standard interference fringe image 34R in which the center point C1 of the interference fringe 33 is positioned are R21 and R42. In this case, in accordance with the required irradiation position table 56, the required irradiation positions corresponding to the region R21 are the irradiation positions IP14, IP15, IP24, IP25, IP34, and IP35. In addition, the required irradiation positions corresponding to the region R42 are the irradiation positions IP33, IP34, IP35, IP43, IP44, IP45, IP53, IP54, and IP55. That is, the irradiation positions IP34 and IP35 overlap as the required irradiation position. The light source control unit 60 causes the light emission unit 41 to emit the coherent light 23 in the order of the irradiation positions IP33, IP43, IP53, IP54, IP44, IP34, IP24, IP14, IP15, IP25, IP35, IP45, and IP55, for example. That is, the light source control unit 60 causes the light emission unit 41 to emit the coherent light 23 only once from the irradiation positions IP34 and IP35, which are the overlapping required irradiation positions.

Figure 21:
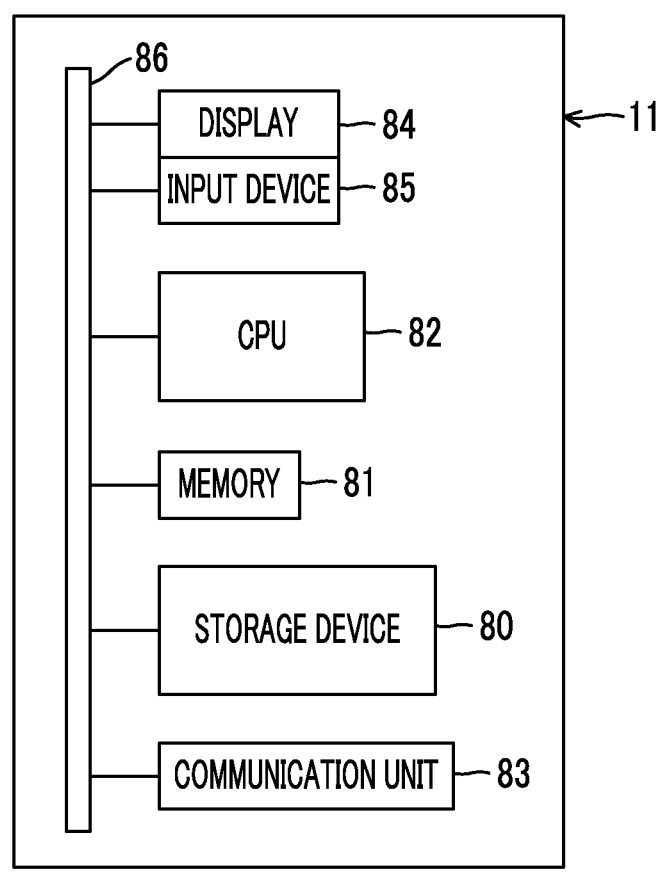
FIG. 21 is a block diagram showing a computer constituting an information processing apparatus.

In FIG. 21, the computer constituting the information processing apparatus 11 comprises a storage device 80, a memory 81, a central processing unit (CPU) 82, a communication unit 83, a display 84, and an input device 85. These components are connected to each other via a bus line 86.

The storage device 80 is a hard disk drive that is built in the computer constituting the information processing apparatus 11 or is connected thereto via a cable or a network. Alternatively, the storage device 80 is a disk array in which a plurality of hard disk drives are mounted. In the storage device 80, a control program, such as an operating system, various application programs, various data associated with such programs, and the like are stored. It should be noted that a solid state drive may be used instead of the hard disk drive.

The memory 81 is a work memory in which the CPU 82 executes processing. The CPU 82 loads the program stored in the storage device 80 to the memory 81 and executes the processing in accordance with the program to comprehensively control the units of the computer.

The communication unit 83 is a network interface that performs a transmission control of various information via a network, such as a local area network (LAN) or a wide area network (WAN). The display 84 displays various screens. The computer constituting the information processing apparatus 11 receives an input of an operation instruction from the input device 85 via the various screens. Examples of the input device 85 include a keyboard, a mouse, and a touch panel.

Figure 22:
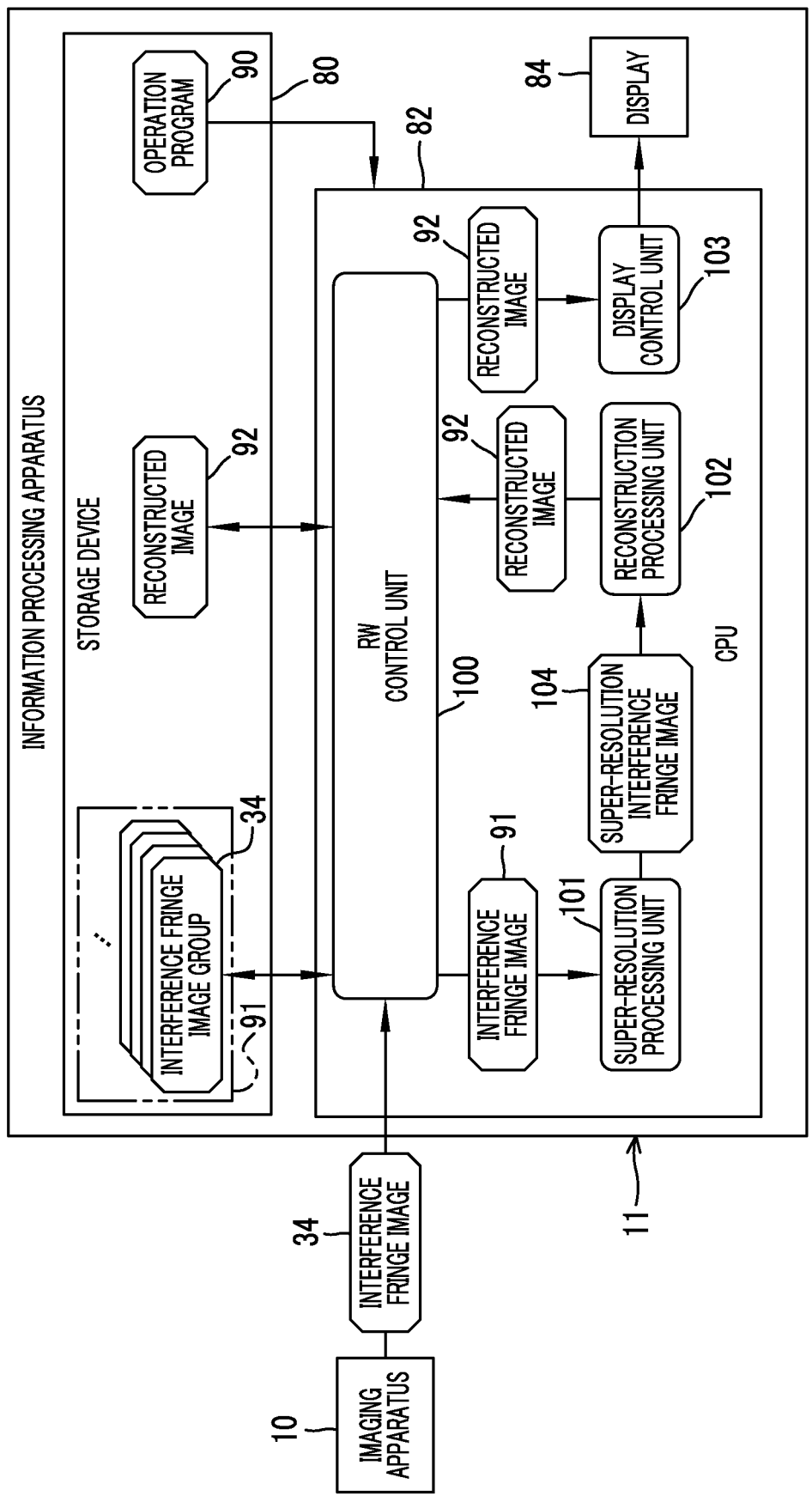
FIG. 22 is a block diagram showing a processing unit of a CPU of the information processing apparatus.

In FIG. 22, an operation program 90 is stored in the storage device 80 of the information processing apparatus 11. An interference fringe image group 91 and a reconstructed image 92 are also stored in the storage device 80. The interference fringe image group 91 is a collection of the plurality of interference fringe images 34 that are the sources of the super-resolution interference fringe image 104 transmitted from the imaging apparatus 10.

In a case in which the operation program 90 is activated, the CPU 82 of the computer constituting the information processing apparatus 11 functions as a read write (hereinafter, abbreviated as RW) control unit 100, a super-resolution processing unit 101, a reconstruction processing unit 102, and a display control unit 103, in cooperation with the memory 81 and the like.

The RW control unit 100 controls storing of various data in the storage device 80 and reading out of the various data in the storage device 80. For example, the RW control unit 100 receives the interference fringe image 34 from the imaging apparatus 10 and stores the received interference fringe image 34 in the storage device 80 as the interference fringe image group 91. In addition, the RW control unit 100 reads out the interference fringe image group 91 from the storage device 80 and outputs the interference fringe image group 91 to the super-resolution processing unit 101.

The super-resolution processing unit 101 generates the super-resolution interference fringe image 104 from the interference fringe image group 91. The super-resolution processing unit 101 outputs the super-resolution interference fringe image 104 to the reconstruction processing unit 102.

The reconstruction processing unit 102 generates the reconstructed image 92 from the super-resolution interference fringe image 104. The reconstruction processing unit 102 outputs the reconstructed image 92 to the RW control unit 100. The RW control unit 100 stores the reconstructed image 92 in the storage device 80. In addition, the RW control unit 100 reads out the reconstructed image 92 from the storage device 80 and outputs the reconstructed image 92 to the display control unit 103.

The display control unit 103 controls display of the various screens on the display 84. The various screens include a reconstructed image display screen 150 (see FIG. 27), which is a screen on which the reconstructed image 92 is displayed.

Figure 23:
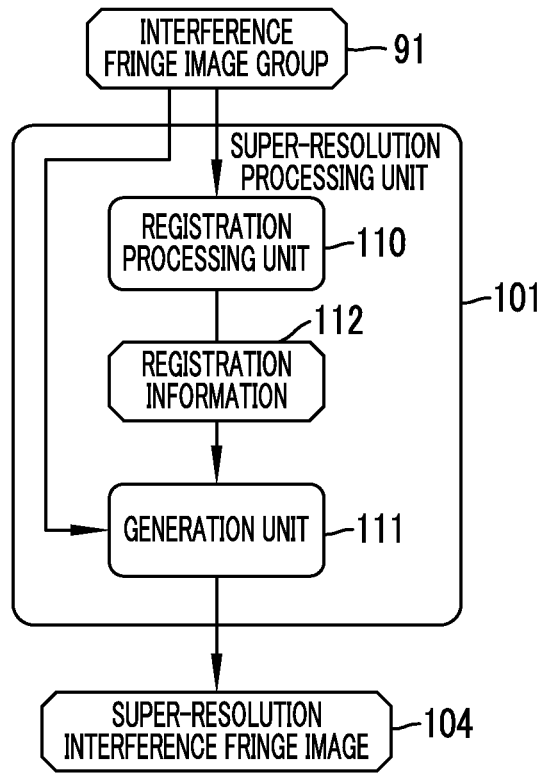
FIG. 23 is a view showing a super-resolution processing unit.

In FIG. 23, the super-resolution processing unit 101 includes a registration processing unit 110 and a generation unit 111. The registration processing unit 110 performs the registration processing outlined in FIG. 9 on the plurality of interference fringe images 34 constituting the interference fringe image group 91. The registration processing unit 110 outputs registration information 112, which is a result of the registration processing, to the generation unit 111.

The generation unit 111 performs the reconstruction processing outlined in FIG. 9 on the plurality of interference fringe images 34 constituting the interference fringe image group 91 with reference to the registration information 112. As a result, the super-resolution interference fringe image 104 is generated.

Figure 24:
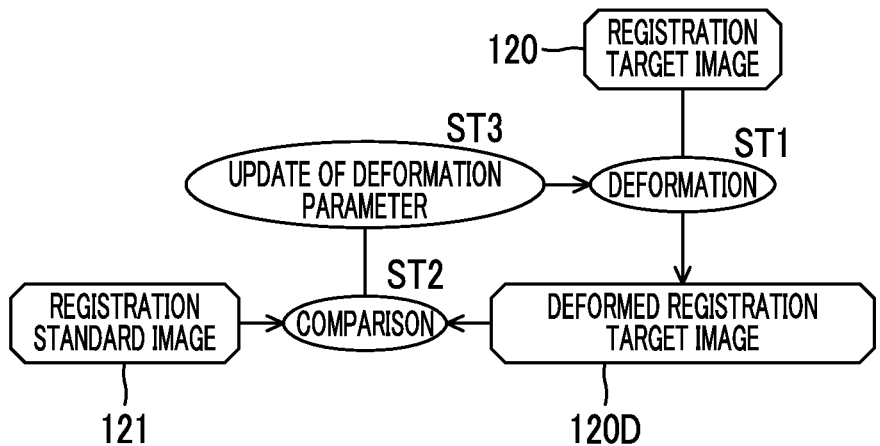
FIG. 24 is a view showing details of registration processing by a registration processing unit.

FIG. 24 is a view showing details of the registration processing by the registration processing unit 110. The registration processing unit 110 performs the registration processing by, for example, region-based matching. First, the registration processing unit 110 applies various deformation parameters, such as parallel translation, rotation, and enlargement/reduction, to a registration target image 120 and deforms the registration target image 120 to obtain a deformed registration target image 120D (step ST1). Then, the deformed registration target image 120D and a registration standard image 121 are compared, and a degree of similarity between the deformed registration target image 120D and the registration standard image 121 is calculated (step ST2). Moreover, the deformation parameters are updated such that the degree of similarity is increased (step ST3). The registration processing unit 110 repeats the processing of steps ST1 to ST3 until the degree of similarity between the deformed registration target image 120D and the registration standard image 121 is equal to or larger than a preset threshold value. The registration processing unit 110 outputs the deformation parameters in a case in which the degree of similarity between the deformed registration target image 120D and the registration standard image 121 is equal to or larger than the threshold value to the generation unit 111 as the registration information 112.

The registration standard image 121 is one of the plurality of interference fringe images 34 constituting the interference fringe image group 91, and the registration target image 120 is the interference fringe image 34 other than the registration standard image 121. The registration standard image 121 is, for example, the interference fringe image 34 obtained in a case in which the coherent light 23 is emitted from the light emission unit 41 at the center point correspondence irradiation position. In the example of FIGS. 15 and 16, the region of the standard interference fringe image 34R in which the center point C1 of the interference fringe 33 is positioned is R14, and the center point correspondence irradiation position corresponding to the region R14 is IP12. Therefore, the interference fringe image 34 obtained in a case in which the coherent light 23 is emitted from the light emission unit 41 of the center point correspondence irradiation position IP12 is the registration standard image 121. In a case in which there are a plurality of interference fringes 33 as in the examples of FIGS. 19 and 20, the registration standard image 121 is the interference fringe image 34 obtained in a case in which the coherent light 23 is emitted from the light emission unit 41 at the center point correspondence irradiation position corresponding to the region R of the standard interference fringe image 34R in which the center point C1 of the interference fringe 33 is positioned, which is the center point correspondence irradiation position closer to the irradiation position IP33 corresponding to the center region R33 (irradiation position IP44 corresponding to the region R42 in cases of FIGS. 19 and 20).

Figure 25:
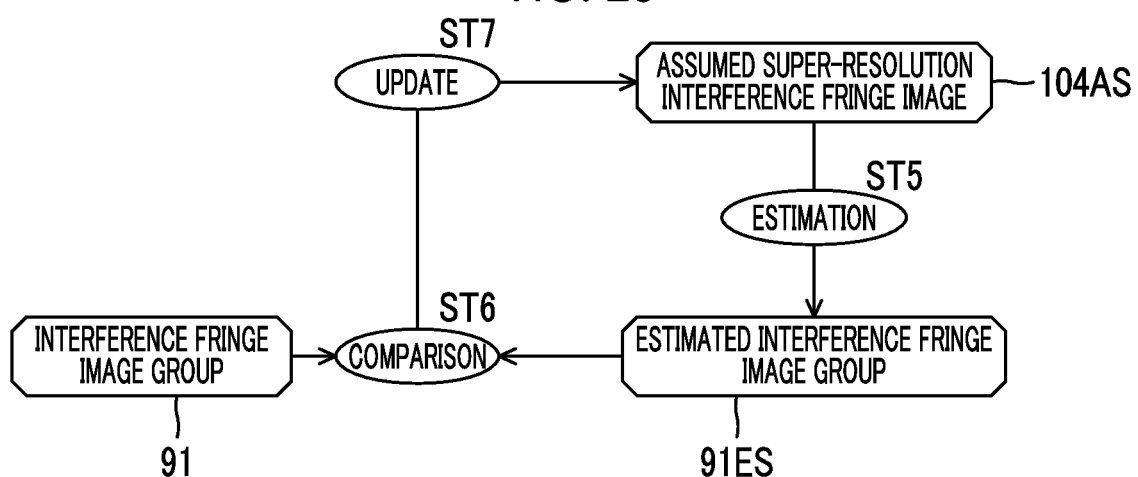
FIG. 25 is a view showing details of reconstruction processing by a reconstruction processing unit.

FIG. 25 is a view showing details of the reconstruction processing by the generation unit 111. The generation unit 111 performs the reconstruction processing based on, for example, a maximum a posteriori (MAP) estimation. First, the generation unit 111 generates an appropriate assumed super-resolution interference fringe image 104AS, and generates an estimated interference fringe image group 91ES from the assumed super-resolution interference fringe image 104AS based on the point spread function (PSF) of the imaging element 22, the registration information 112, and the like (step ST5). Then, the estimated interference fringe image group 91ES and the actual interference fringe image group 91 are compared (step ST6). Moreover, the assumed super-resolution interference fringe image 104AS is updated such that a difference between the estimated interference fringe image group 91ES and the actual interference fringe image group 91 is reduced (step ST7). The generation unit 111 repeats the processing of steps ST5 to ST7 until the difference between the estimated interference fringe image group 91ES and the actual interference fringe image group 91 is less than a preset threshold value. The generation unit 111 outputs the assumed super-resolution interference fringe image 104AS in a case in which a difference between the estimated interference fringe image group 91ES and the actual interference fringe image group 91 is less than the threshold value, as the final super-resolution interference fringe image 104.

Figure 26:
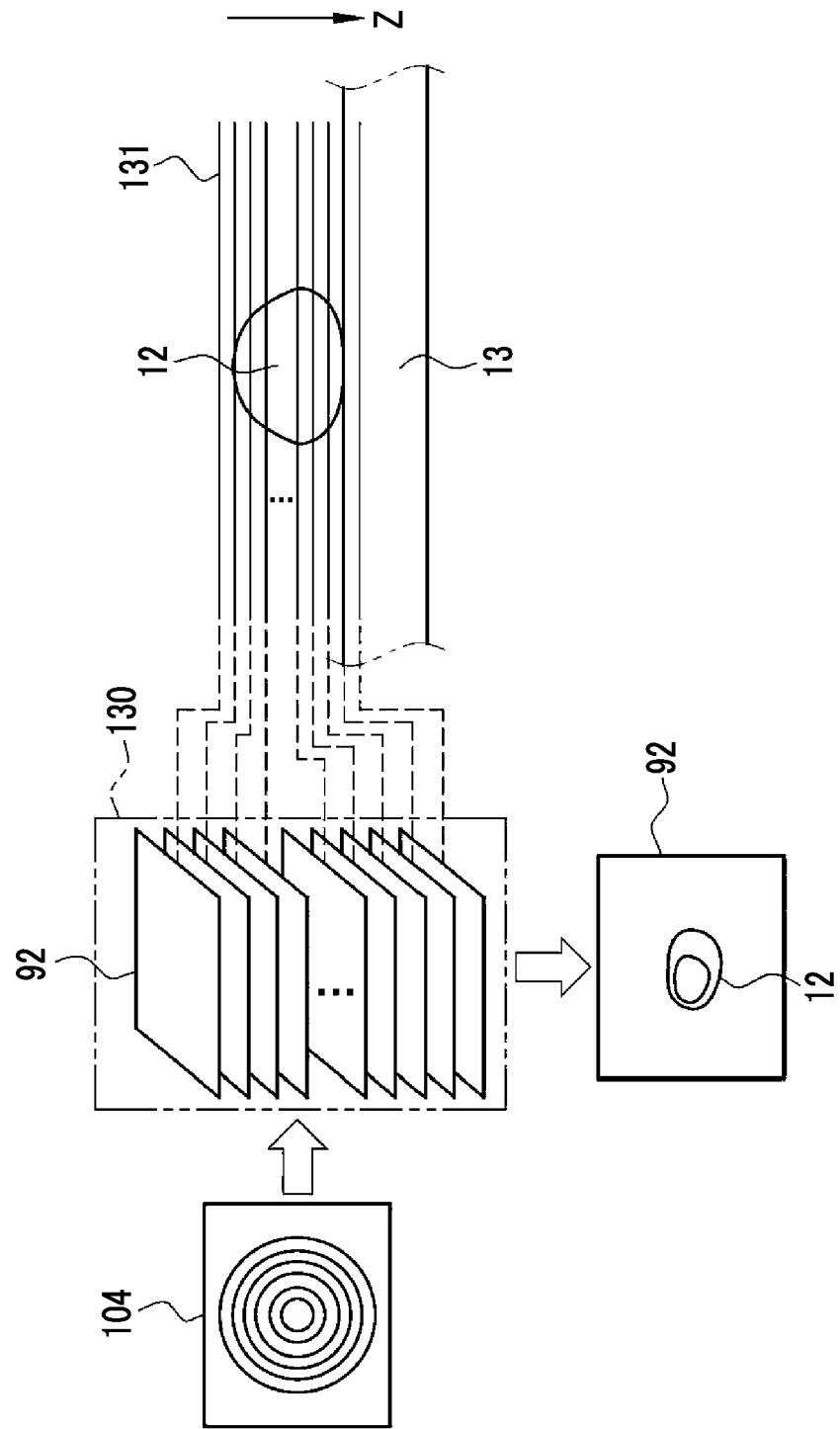
FIG. 26 is a view showing an outline of operation processing by a generation unit.

FIG. 26 is a view showing an outline of operation processing by the reconstruction processing unit 102. First, the reconstruction processing unit 102 reconstructs the super-resolution interference fringe image 104 to generate the reconstructed image 92. A reconstructed image group 130 is a collection of a plurality of reconstructed images 92. These plurality of reconstructed images 92 are images representing tomographic planes 131 arranged at equal intervals in a thickness direction of the cell 12 and the culture container 13 along the Z direction, respectively.

The reconstruction processing unit 102 selects one reconstructed image 92 that is most in focus from among the plurality of reconstructed images 92 of the reconstructed image group 130. The reconstruction processing unit 102 outputs the selected reconstructed image 92 to the RW control unit 100. It should be noted that, as a method of selecting the reconstructed image 92 that is most in focus, a method can be adopted in which a contrast value of each of the plurality of reconstructed images 92 is calculated, and the reconstructed image 92 having the highest contrast value is selected as the reconstructed image 92 that is most in focus.

Figure 27:
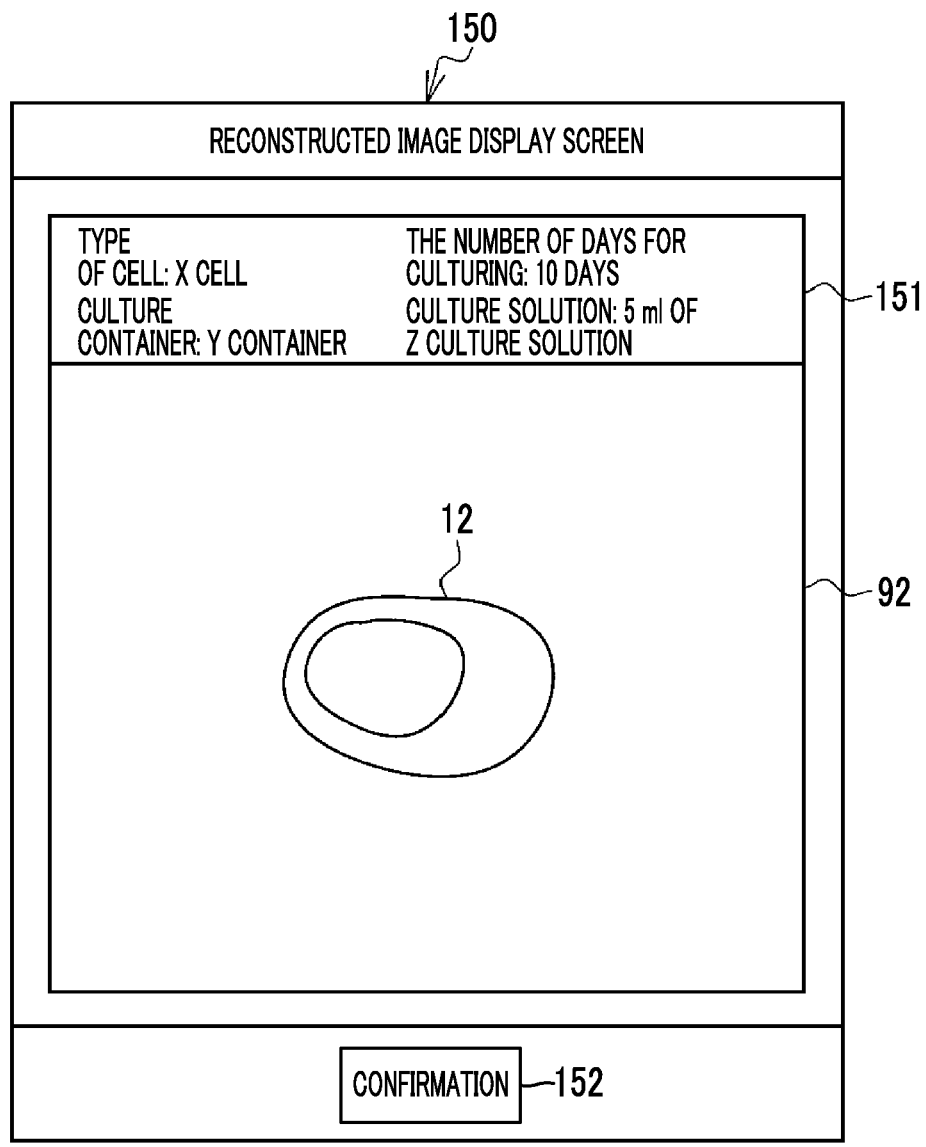
FIG. 27 is a view showing a reconstructed image display screen.

As shown in FIG. 27, the reconstructed image 92 is displayed on the reconstructed image display screen 150 together with type information 151. The type information 151 includes the type of the cell 12, the number of days for culturing the cell 12, the type of the culture container 13, the type of a culture solution, and a usage amount of the culture solution. The display of the reconstructed image display screen 150 disappears in a case in which a confirmation button 152 is selected.

Next, the actions of the configuration described above will be described with reference to the flowcharts of FIGS. 28 and 29. First, in a case in which the operation program 55 is activated by the imaging apparatus 10, as shown in FIG. 10, the CPU 52 of the imaging apparatus 10 functions as the light source control unit 60, the imaging control unit 61, the acquisition unit 62, the setting unit 63, and the transmission control unit 64.

Figure 28:
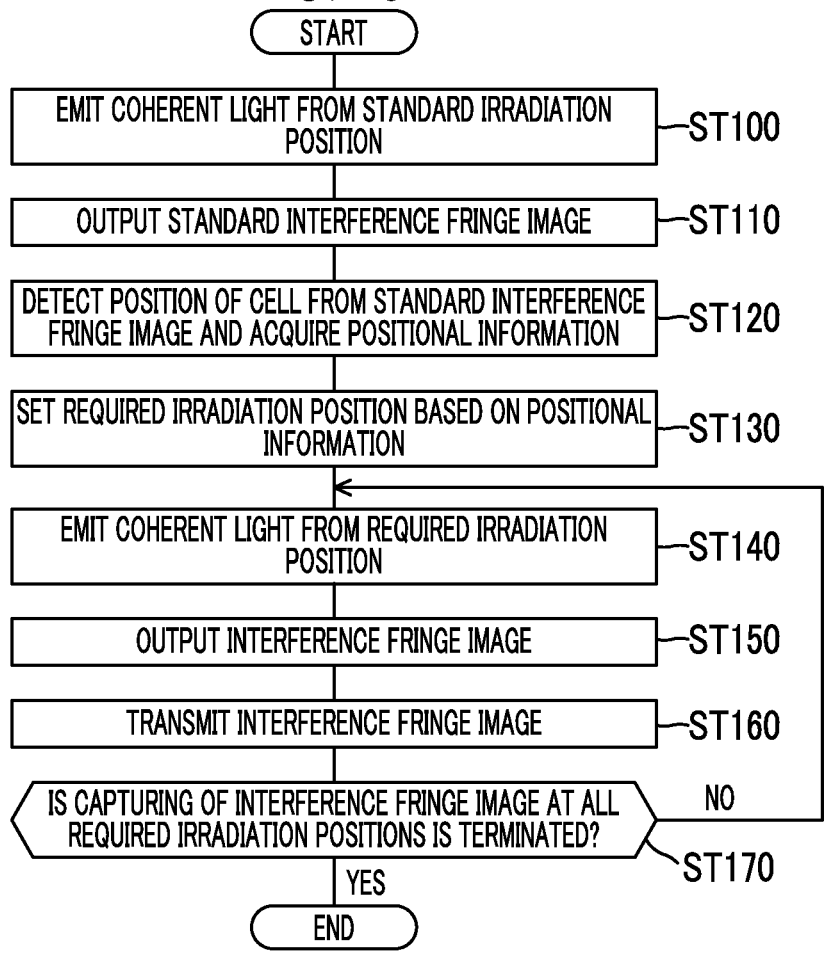
FIG. 28 is a flowchart showing a processing procedure of the imaging apparatus.

In FIG. 28, first, under the control of the light source control unit 60, the coherent light 23 is emitted from the light emission unit 41 at the irradiation position IP33, which is the standard irradiation position, as shown in FIG. 11 (step ST100). Moreover, the interference fringe 33 generated by the irradiation is imaged by the imaging element 22 under the control of the imaging control unit 61, and the standard interference fringe image 34R is output from the imaging element 22 (step ST110). The standard interference fringe image 34R is input to the acquisition unit 62.

As shown in FIG. 12, the acquisition unit 62 detects the position of the center point C1 of the interference fringe 33 from the standard interference fringe image 34R as the position of the cell 12. As a result, the positional information 70 is acquired by the acquisition unit 62 (step ST120). The positional information 70 is output to the setting unit 63 from the acquisition unit 62. It should be noted that step ST120 is an example of an "acquisition step" according to the technology of the present disclosure.

In the setting unit 63, as shown in FIGS. 15 to 20, the required irradiation position is set from among the plurality of irradiation positions IP11 to IP55 based on the required irradiation position table 56 and the positional information 70 (step ST130). Moreover, the setting information 71 indicating the required irradiation position is generated. The setting information 71 is output to the light source control unit 60 from the setting unit 63. It should be noted that step ST130 is an example of a "setting step" according to the technology of the present disclosure.

Under the control of the light source control unit 60, the coherent light 23 is emitted from the light emission unit 41 at the required irradiation position indicated by the setting information 71 (step ST140). Moreover, the interference fringe 33 generated by the irradiation is imaged by the imaging element 22 under the control of the imaging control unit 61, and the interference fringe image 34 is output from the imaging element 22 (step ST150). In this case, as shown in FIGS. 19 and 20, in a case in which there are a plurality of cells 12 and the required irradiation positions of the plurality of cells 12 overlap, the coherent light 23 is emitted only once from the overlapping required irradiation positions. It should be noted that step ST140 is an example of a "light source control step" according to the technology of the present disclosure. In addition, step ST150 is an example of an "imaging control step" according to the technology of the present disclosure.

The interference fringe image 34 is input to the transmission control unit 64 and transmitted to the information processing apparatus 11 by the transmission control unit 64 (step ST160). These steps ST140 to ST160 are repeated while capturing of the interference fringe image 34 at all the required irradiation positions is not terminated (NO in step ST170). In a case in which capturing of the interference fringe image 34 at all the required irradiation positions is terminated (YES in step ST170), the repetitive processing of steps ST140 to ST160 is terminated.

First, in a case in which the operation program 90 is activated by the information processing apparatus 11, as shown in FIG. 22, the CPU 82 of the information processing apparatus 11 functions as the RW control unit 100, the super-resolution processing unit 101, the reconstruction processing unit 102, and the display control unit 103.

The information processing apparatus 11 receives the interference fringe image 34 from the imaging apparatus 10. The interference fringe image 34 is stored in the storage device 80 by the RW control unit 100. As a result, the interference fringe image group 91 is stored in the storage device 80.

Figure 29:
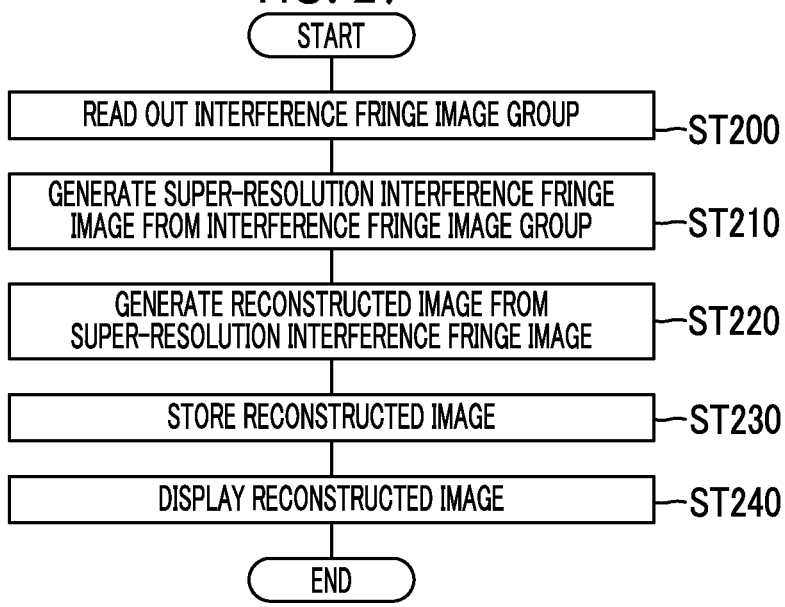
FIG. 29 is a flowchart showing a processing procedure of the information processing apparatus.

In FIG. 29, the RW control unit 100 reads out the interference fringe image group 91 from the storage device 80 (step ST200). The interference fringe image group 91 is output to the super-resolution processing unit 101 from the RW control unit 100.

As shown in FIGS. 23 to 25, the super-resolution processing unit 101 performs the registration processing and the reconstruction processing to generate the super-resolution interference fringe image 104 from the interference fringe image group 91 (step ST210). The super-resolution interference fringe image 104 is output to the reconstruction processing unit 102 from the super-resolution processing unit 101.

As shown in FIG. 26, the reconstruction processing unit 102 generates the reconstructed image 92 from the super-resolution interference fringe image 104 (step ST220). The reconstructed image 92 is output to the RW control unit 100 from the reconstruction processing unit 102, and is stored in the storage device 80 by the RW control unit 100 (step ST230).

The RW control unit 100 reads out the reconstructed image 92 from the storage device 80. The reconstructed image 92 is output to the display control unit 103 from the RW control unit 100. Moreover, as shown in FIG. 27, the display control unit 103 displays the reconstructed image display screen 150 on the display 84, and the reconstructed image 92 is provided for viewing by a user (step ST240).

As described above, the control device 68 of the imaging apparatus 10 comprises the acquisition unit 62, the setting unit 63, the light source control unit 60, and the imaging control unit 61. The acquisition unit 62 acquires the positional information 70 indicating the position of the cell 12, which is the observation target. The setting unit 63 sets the required irradiation position from among the plurality of irradiation positions IP11 to IP55. The required irradiation position is the irradiation position corresponding to the position of the cell 12 indicated by the positional information 70, and is the irradiation position required for obtaining the plurality of interference fringe images 34 which are sources of the super-resolution interference fringe image 104 having the resolution exceeding the resolution of the imaging element 22. The light source control unit 60 controls the operation of the light source 20 to emit the coherent light 23 from the required irradiation position. The imaging control unit 61 causes the imaging element 22 to output the interference fringe image 34 at each required irradiation position. Therefore, the interference fringe image 34, which has almost no contribution to super-resolution, is not captured. Therefore, it is possible to obtain the super-resolution interference fringe image 104 without wasteful labor.

The acquisition unit 62 acquires the positional information 70 by detecting the position of the cell 12 from the standard interference fringe image 34R which is the interference fringe image 34 obtained by emitting the coherent light 23 from one preset standard irradiation position IP33 among the plurality of irradiation positions IP11 to IP55. Therefore, it is possible to acquire the positional information 70 without bothering the user.

In a case in which there are the plurality of cells 12 and the required irradiation positions of the plurality of cells 12 overlap, the light source control unit 60 causes the light emission unit 41 to emit the coherent light 23 only once from the overlapping required irradiation positions. Therefore, it is possible to save labor of emitting the coherent light 23 many times from the overlapping required irradiation positions and capturing the plurality of substantially the same interference fringe images 34, so that the super-resolution interference fringe image 104 can be obtained in a shorter time.

The field of cell culture has recently been in the limelight with the advent of induced pluripotent stem (iPS) cells and the like. Therefore, there is a demand for the technology of analyzing the cell 12 in culture in detail without wasteful time. In the technology of the present disclosure, the observation target is the cell 12 in culture. Therefore, it can be said that the technology of the present disclosure is the technology that can meet recent demands.

Figure 30:
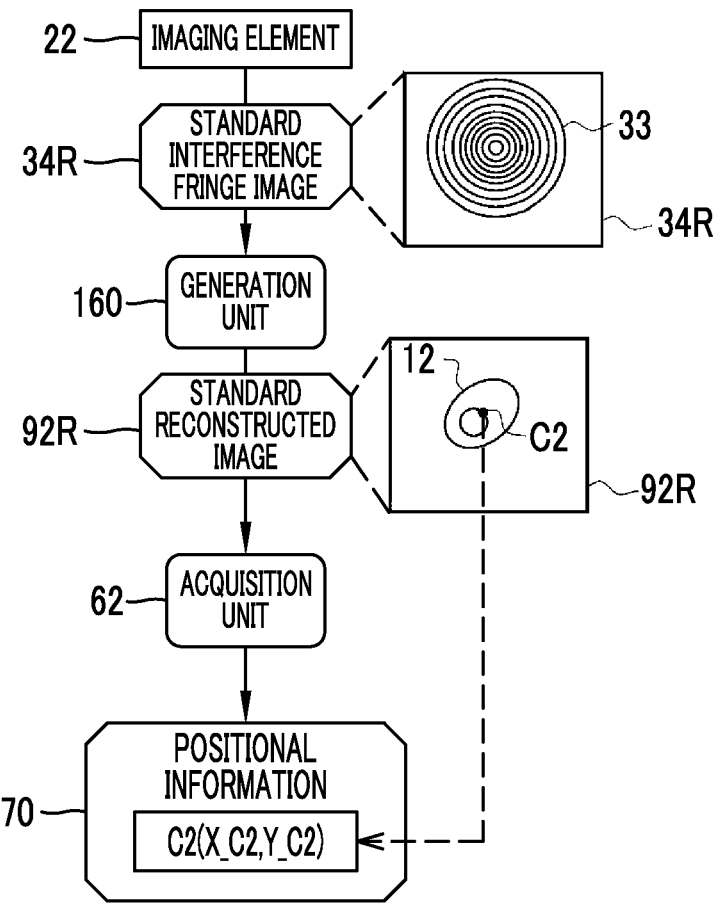
FIG. 30 is a view showing an aspect in which the position of the cell is detected from a standard reconstructed image.

It should be noted that the acquisition unit 62 acquires the positional information 70 by detecting the position of the cell 12 from the standard interference fringe image 34R, but the technology of the present disclosure is not limited to this. As shown in FIG. 30, the acquisition unit 62 may acquire the positional information 70 by detecting the position of the cell 12 from a standard reconstructed image 92R, which is the reconstructed image 92 generated based on the standard interference fringe image 34R, instead of the standard interference fringe image 34R.

In this case, the CPU 52 of the imaging apparatus 10 also functions as a generation unit 160 in addition to the units 60 to 64 shown in FIG. 10 (only the acquisition unit 62 is shown in FIG. 30). The generation unit 160 has the same function as the reconstruction processing unit 102 of the information processing apparatus 11. The generation unit 160 generates the standard reconstructed image 92R from the standard interference fringe image 34R in the same way that the reconstruction processing unit 102 generates the reconstructed image 92 from the super-resolution interference fringe image 104. The generation unit 160 outputs the standard reconstructed image 92R to the acquisition unit 62.

The acquisition unit 62 performs the image analysis on the standard reconstructed image 92R and detects a position of a center point C2 of the cell 12 reflected in the standard reconstructed image 92R as the position of the cell 12, for example. The acquisition unit 62 outputs a position coordinate (X_C2, Y_C2) of the center point C2 of the cell 12 to the setting unit 63 as the positional information 70.

The interference fringe 33 is generated due to dust and the like in the culture solution in addition to the cell 12. Therefore, in a case in which the position of the center point C1 of the interference fringe 33 reflected in the standard interference fringe image 34R is detected as the position of the cell 12, there is a considerable possibility that dust or the like is erroneously recognized as the cell 12. Therefore, as shown in FIG. 30, it is preferable to detect the position of the cell 12 from the standard reconstructed image 92R generated based on the standard interference fringe image 34R, instead of the standard interference fringe image 34R. It should be noted that it takes labor to generate the standard reconstructed image 92R from the standard interference fringe image 34R. Therefore, in a case in which the reduction of such labor is considered first, it is better to adopt the method of detecting the position of the cell 12 from the standard interference fringe image 34R.

Figure 31:
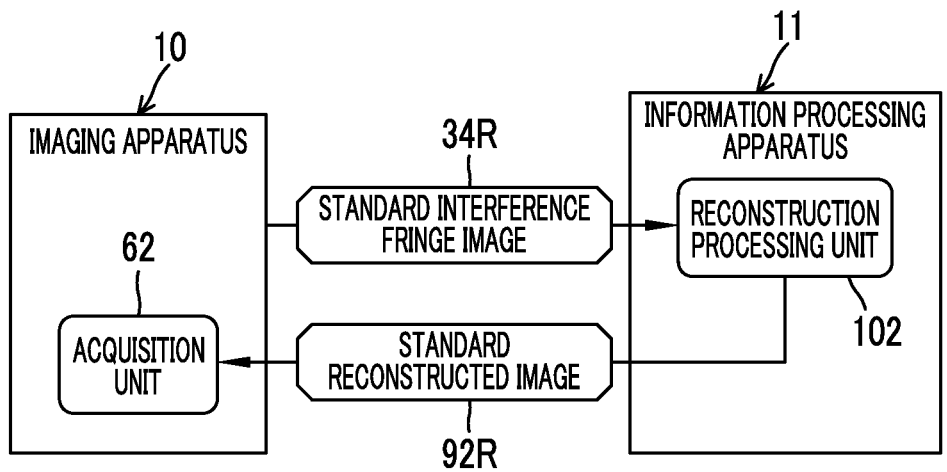
FIG. 31 is a view showing another aspect in which the position of the cell is detected from the standard reconstructed image.

It should be noted that an aspect shown in FIG. 31 may be adopted. That is, the standard interference fringe image 34R is transmitted from the imaging apparatus 10 to the information processing apparatus 11, and the reconstruction processing unit 102 of the information processing apparatus 11 generates the standard reconstructed image 92R from the standard interference fringe image 34R. Moreover, the standard reconstructed image 92R is transmitted from the information processing apparatus 11 to the imaging apparatus 10. In this way, it is not necessary to provide the generation unit 160 in the imaging apparatus 10.

Second Embodiment

The aspect in which the positional information 70 is acquired is not limited to the aspect in which the position of the cell 12 is detected from the standard interference fringe image 34R or the standard reconstructed image 92R, which has been described in the first embodiment. A second embodiment shown in FIGS. 32 and 35 may be adopted.

Figure 32:
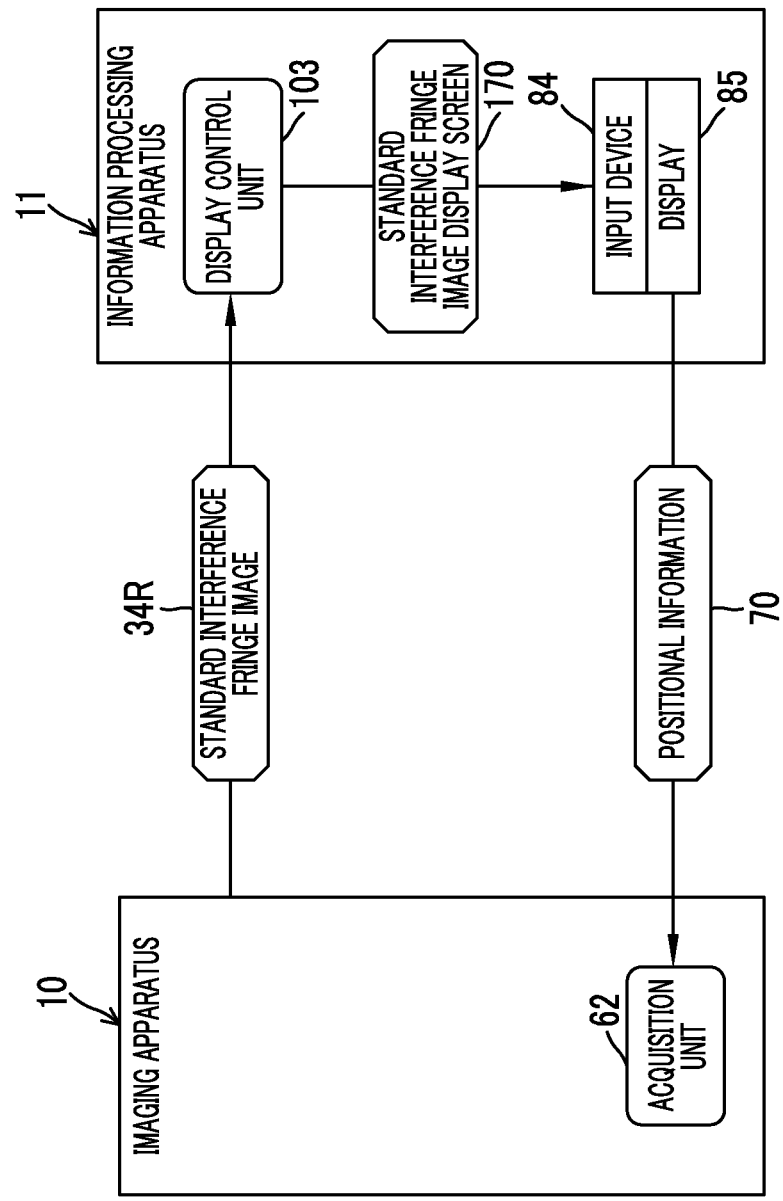
FIG. 32 is a view showing an aspect in which a standard interference fringe image display screen is displayed and the position of the cell is designated on the standard interference fringe image display screen.

In FIG. 32, the imaging apparatus 10 transmits the standard interference fringe image 34R to the information processing apparatus 11. The display control unit 103 of the information processing apparatus 11 performs a control of displaying a standard interference fringe image display screen 170 (see also FIG. 33), which is the display screen of the standard interference fringe image 34R, on the display 84. Moreover, on the standard interference fringe image display screen 170, the user is made to designate the position of the cell 12 via the input device 85. The information processing apparatus 11 generates the positional information 70 based on the designation of the position of the cell 12 on the standard interference fringe image display screen 170, and transmits the generated positional information 70 to the imaging apparatus 10. The acquisition unit 62 acquires the positional information 70 from the information processing apparatus 11.

Figure 33:
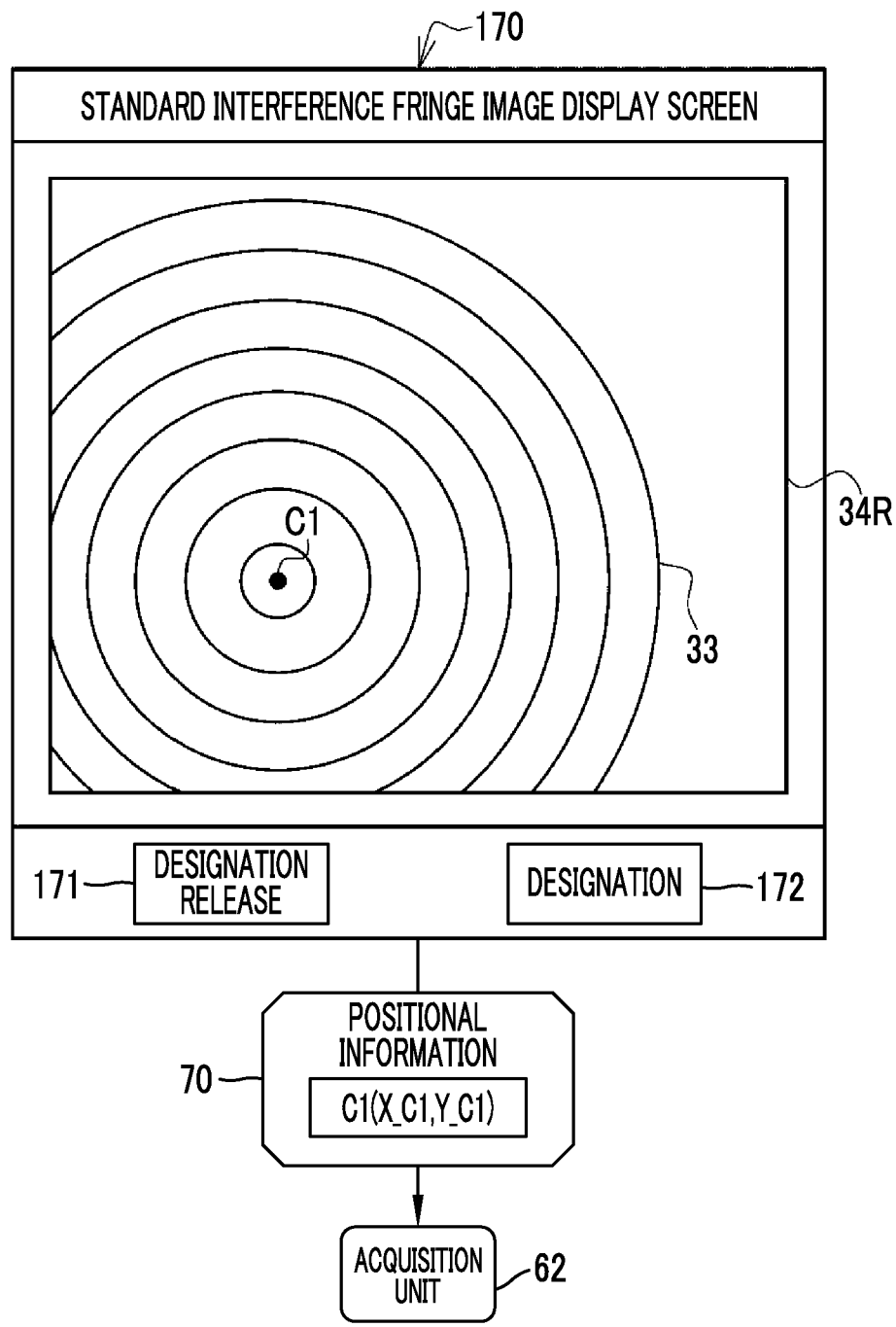
FIG. 33 is a view showing the standard interference fringe image display screen.

As shown in FIG. 33, the standard interference fringe image 34R is displayed on the standard interference fringe image display screen 170, and a designation release button 171 and a designation button 172 are provided below the standard interference fringe image 34R. The center point C1 of the interference fringe 33, which is the position of the cell 12, can be input by, for example, moving the mouse cursor of the input device 85 to a desired position on the standard interference fringe image 34R and double-clicking the mouse. In a case in which the designation release button 171 is selected, the designation of the center point C1 of the most recently designated interference fringe 33 is released. In a case in which the designation button 172 is selected, the position coordinate (X_C1, Y_C1) of the center point C1 of the interference fringe 33 designated in that case is acquired by the acquisition unit 62 as the positional information 70.

Figure 34:
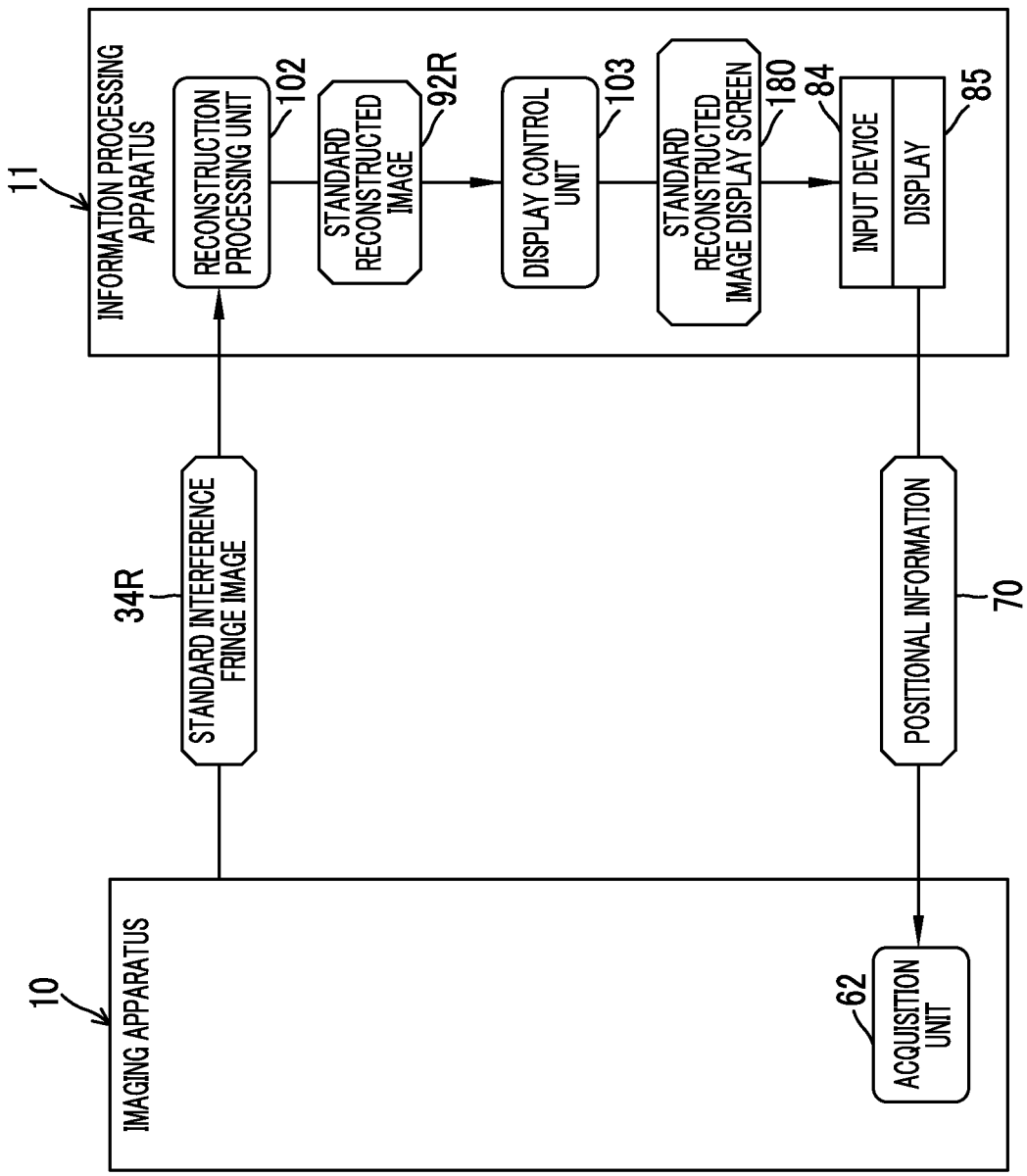
FIG. 34 is a view showing an aspect in which a standard reconstructed image display screen is displayed and the position of the cell is designated on the standard reconstructed image display screen.

FIG. 34 is an example in which the standard reconstructed image 92R is used instead of the standard interference fringe image 34R. In this case, the reconstruction processing unit 102 of the information processing apparatus 11 generates the standard reconstructed image 92R from the standard interference fringe image 34R. The reconstruction processing unit 102 outputs the standard reconstructed image 92R to the display control unit 103. The display control unit 103 performs a control of displaying a standard reconstructed image display screen 180 (see also FIG. 35), which is the display screen of the standard reconstructed image 92R, on the display 84. Moreover, on the standard reconstructed image display screen 180, the user is made to designate the position of the cell 12 via the input device 85. The information processing apparatus 11 generates the positional information 70 based on the designation of the position of the cell 12 on the standard reconstructed image display screen 180, and transmits the generated positional information 70 to the imaging apparatus 10. The acquisition unit 62 acquires the positional information 70 from the information processing apparatus 11.

Figure 35:
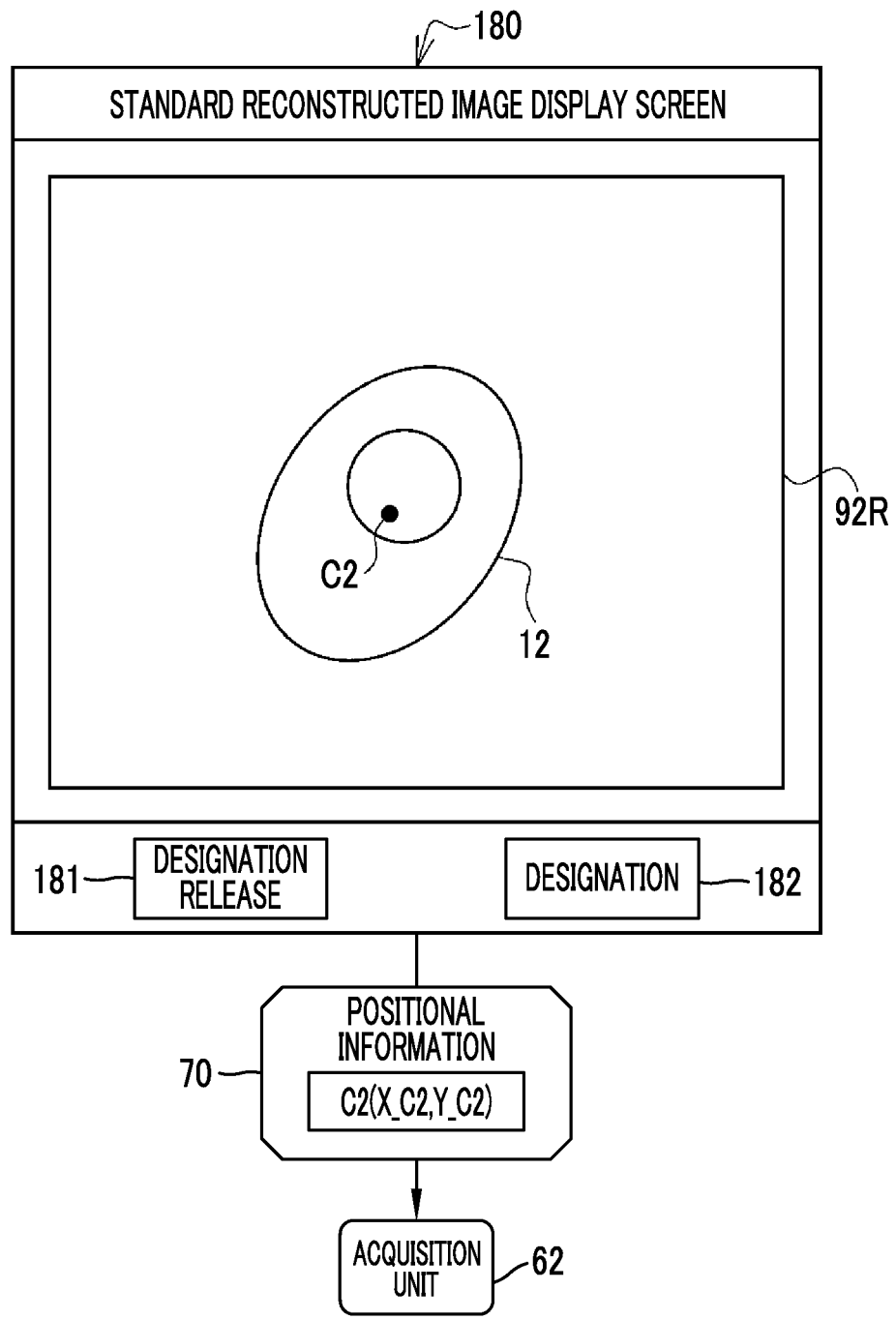
FIG. 35 is a view showing the standard reconstructed image display screen.

As shown in FIG. 35, the standard reconstructed image 92R is displayed on the standard reconstructed image display screen 180, and a designation release button 181 and a designation button 182 are provided below the standard reconstructed image 92R. The center point C2 of the cell 12, which is the position of the cell 12, can be input by moving the mouse cursor of the input device 85 to a desired position on the standard reconstructed image 92R and double-clicking the mouse, as in a case of the standard interference fringe image display screen 170. In a case in which the designation release button 181 is selected, the designation of the center point C2 of the most recently designated cell 12 is released as in a case of the designation release button 171. In a case in which the designation button 182 is selected, the position coordinate (X_C2, Y_C2) of the center point C2 of the cell 12 designated in that case is acquired by the acquisition unit 62 as the positional information 70, as in a case of the designation button 172.

As described above, in the second embodiment, the display control unit 103 of the information processing apparatus 11 performs a control of displaying the standard interference fringe image display screen 170 shown in FIGS. 32 and 33, or the standard reconstructed image display screen 180 shown in FIGS. 34 and 35. The acquisition unit 62 acquires the positional information 70 by receiving the designation of the position of the cell 12 on the standard interference fringe image display screen 170 or the standard reconstructed image display screen 180. Therefore, it is possible to acquire the more probable positional information 70 designated by the user himself/herself.

It should be noted that, in the second embodiment, the control device according to the present disclosure is realized by the light source control unit 60, the imaging control unit 61, the acquisition unit 62, the setting unit 63, and the display control unit 103 of the information processing apparatus 11. As described above, the processing unit constituting the control device may be provided in the information processing apparatus 11, in addition to the imaging apparatus 10.

Third Embodiment

In a third embodiment shown in FIGS. 36 and 37A to 37C, the number of required irradiation positions is changed in accordance with size information 190 indicating a size of the cell 12.

Figure 36:
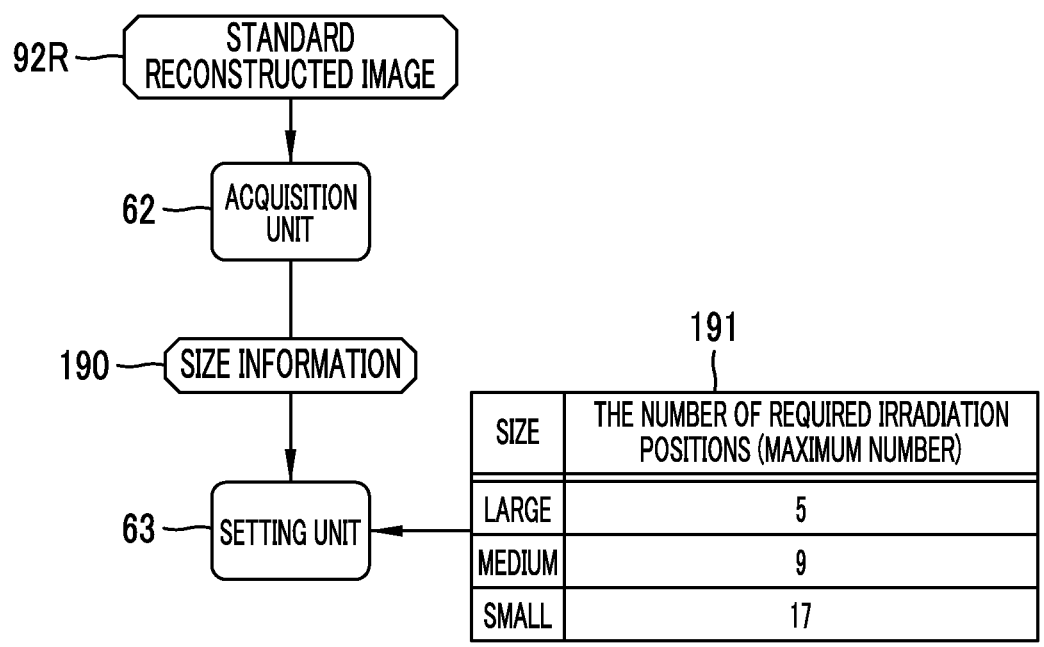
FIG. 36 is a view showing a third embodiment in which the number of required irradiation positions is changed in accordance with size information indicating a size of the cell.

As shown in FIG. 36, the acquisition unit 62 performs the image analysis on the standard reconstructed image 92R and counts the number of pixels of the cell 12 reflected in the standard reconstructed image 92R, for example. Moreover, three sizes of large, medium, and small, are assigned to the cell 12 in accordance with the number of counted pixels. In a case in which there are the plurality of cells 12, the number of pixels of each of the plurality of cells 12 is counted, and the size is assigned to the cell 12 having the smallest number of counted pixels as a representative. As a result, the acquisition unit 62 acquires the size information 190 indicating the size of the cell 12. The acquisition unit 62 outputs the size information 190 to the setting unit 63.

The setting unit 63 changes the number of required irradiation positions in accordance with the size information 190. Specifically, as shown in a required irradiation position number table 191, in a case in which the size of the cell 12 is large, the number of required irradiation positions is five, in a case in which the size of the cell 12 is medium, the number of required irradiation positions is nine, and in a case in which the size of the cell 12 is small, the number of required irradiation positions is 17. As described above, the number of required irradiation positions is set to larger as the size of the cell 12 is smaller. The reason for increasing the number of required irradiation positions as the size of the cell 12 is smaller is that, as the size of the cell 12 is smaller, the limit of the resolution of the imaging element 22 is closer and it is more difficult to obtain the clear interference fringe image 34.

FIGS. 37A to 37C show the required irradiation positions in a case in which the region of the standard interference fringe image 34R in which the center point C1 of the interference fringe 33 is positioned is R33. FIG. 37A shows a case in which the size of the cell 12 is large, FIG. 37B shows a case in which the size of the cell 12 is medium, and FIG. 37C shows a case in which the size of the cell 12 is small. In a case in which the size of the cell 12 in FIG. 37A is large, the required irradiation positions are a total of five irradiation positions IP22, IP24, IP33, IP42, and IP44. In a case in which the size of the cell 12 in FIG. 37B is medium, the required irradiation positions are a total of nine irradiation positions IP22, IP23, IP24, IP32, IP33, IP34, IP42, IP43, and IP44. In a case in which the size of the cell 12 in FIG. 37C is small, the required irradiation positions are a total of 17 irradiation positions IP11, IP13, IP15, IP22, IP23, IP24, IP31, IP32, IP33, IP34, IP35, IP42, IP43, IP44, IP51, IP53, and IP55.

As described above, in the third embodiment, the acquisition unit 62 acquires the size information 190 indicating the size of the cell 12, in addition to the positional information 70. The setting unit 63 changes the number of required irradiation positions in accordance with the size information 190. Therefore, it is possible to obtain the number of interference fringe images 34 adapted to the size of the cell 12, and it is possible to generate the super-resolution interference fringe image 104 adapted to the size of the cell 12.

It should be noted that the size of the cell 12 is not limited to the three stages of large, medium, and small. The size of the cell 12 may be two stages, small and other. Alternatively, the size of the cell 12 may be divided into three stages. In addition, the number of required irradiation positions to be changed is not limited to the five, nine, and 17 described above. In a case of the size of large, the required irradiation position may be set to only one not to generate the super-resolution interference fringe image 104 itself.

Fourth Embodiment

In each of the embodiments described above, the light source 20 having the configuration in which the plurality of light emission units 41 are arranged at the plurality of irradiation positions IP11 to IP55 has been described, but the technology of the present disclosure is not limited to this. A fourth embodiment shown in FIGS. 38 and 39 may be adopted.

In FIG. 38, a light source 200 includes one light emission unit 201, a moving stage 202, and a moving mechanism 203. The light emission unit 201 is moved on the moving stage 202 by the moving mechanism 203. The moving mechanism 203 includes, for example, a motor and a rack and pinion gear that converts the rotation of the motor into translational motion along the X direction and the Y direction. The moving mechanism 203 moves the light emission unit 201 in the X direction and the Y direction under the control of the light source control unit 60, and guides the light emission unit 201 to the 5×5=25 irradiation positions IP11 to IP55.

Even with the light source 200 having such a configuration, it is possible to emit the coherent light 23 from the plurality of irradiation positions IP11 to IP55 having different irradiation angles. It should be noted that the configuration becomes complicated due to the moving stage 202 and the moving mechanism 203. In addition, since the light emission unit 201 should be moved to each required irradiation position, an imaging interval of the plurality of interference fringe images 34 is longer than that of the light source 20 of each of the embodiments described above. In a case in which the imaging interval is longer, the cell 12 may be moved during imaging. Therefore, the light source 20 of each of the embodiments described above is more preferable.

It should be noted that the number of light emission units 201 that moves the moving stage 202 is not limited to one, and may be plurality. In addition, for example, as shown in FIG. 39, the light source 210 having a configuration in which 2×2=4 light emission units 211 are arranged may be moved in the X direction and the Y direction by a moving mechanism 212.

In the light sources 20, 200, and 210 shown in each of the embodiments described above, the light emission units 41, 201, and 211 are arranged in parallel with the imaging surface 32, but the technology of the present disclosure is not limited to this. For example, a light source 220 shown in FIG. 40 may be used.

Figure 40:
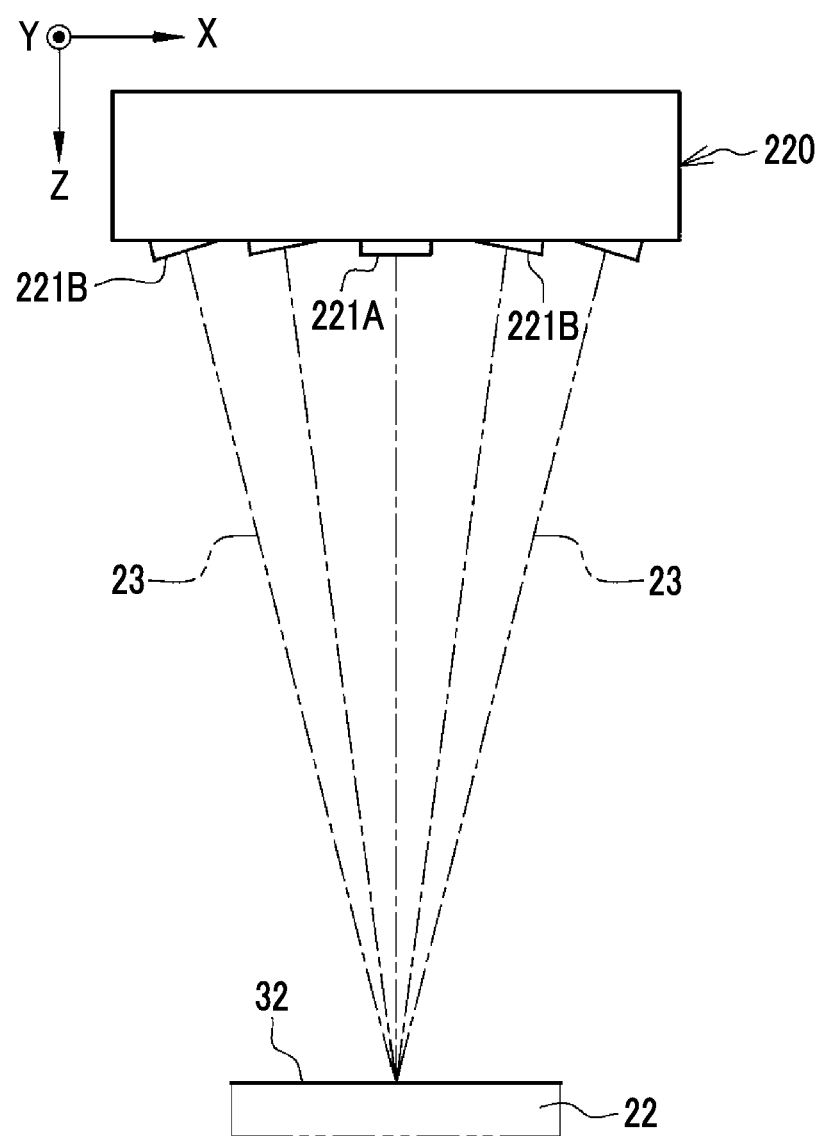
FIG. 40 is a view showing still another example of the light source.

In FIG. 40, in the light source 220, a light emission unit 221B other than a center light emission unit 221A is disposed to be inclined with respect to the imaging surface 32. An inclined angle of the light emission unit 221B is increased toward the end. In addition, the inclined angle of the light emission unit 221B at a symmetrical position with respect to the light emission unit 221A is the same. It should be noted that a configuration may be adopted in which the light emission unit 221B is movable and the inclined angle of the light emission unit 221B is changeable.

The standard interference fringe image 34R may be diverted to generate the super-resolution interference fringe image 104.

The light emission unit may be, for example, a distal end of an optical fiber that is connected to a laser diode that emits the coherent light 23 and guides the coherent light 23. In addition, the irradiation angle of the coherent light 23 may vary by swinging the light emission unit around an axis along the X direction or the Y direction. In this case, a swing position of the light emission unit corresponds to the irradiation position.

The irradiation position is not limited to the 5×5=25 positions described above. The irradiation position can be appropriately changed in accordance with the size of the pixel 45 of the imaging element 22, the size of the cell 12, and the like.

The observation target is not limited to the cell 12 described above. Bacteria, viruses and the like may be the observation target. In addition, the diffracted light is not limited to the diffracted light 30 transmitted through the observation target, and may be diffracted light reflected by the observation target. Further, the coherent light 23 from the light source 20 may be split into two beams for diffracted light and one for reference light to irradiate the observation target with each light. In addition, the illumination light does not have to be the coherent light 23, and need only be any light that generates the interference fringe 33 that can withstand observation.

A hardware configuration of the computer constituting the control device can be modified in various ways. For example, the control device can be composed of a plurality of computers separated as hardware in order to improve processing capacity and reliability. Specifically, the functions of the light source control unit 60 and the imaging control unit 61 and the functions of the acquisition unit 62 and the setting unit 63 are distributed and assigned to two computers. In this case, the two computers constitutes the control device. It should be noted that the two computers may be the imaging apparatus 10 and the information processing apparatus 11. For example, the functions of the light source control unit 60 and the imaging control unit 61 are assigned to the imaging apparatus 10, and the functions of the acquisition unit 62 and the setting unit 63 are assigned to the information processing apparatus 11, respectively. All the functions of the light source control unit 60, the imaging control unit 61, the acquisition unit 62, and the setting unit 63 may be assigned to the information processing apparatus 11.

As described above, the hardware configuration of the computer of the imaging control device can be appropriately changed in accordance with required performance, such as processing capacity, safety, and reliability. Further, in addition to the hardware, the application programs, such as the operation programs 55 and 90, can be duplicated or distributed to a plurality of storage devices for the purpose of ensuring safety and reliability.

In each of the embodiments described above, for example, the following various processors can be used as a hardware structure of processing units that executes various pieces of processing, such as the light source control unit 60, the imaging control unit 61, the acquisition unit 62, the setting unit 63, the transmission control unit 64, the RW control unit 100, the super-resolution processing unit 101 (registration processing unit 110 and generation unit 111), the reconstruction processing units 102 and 160, and the display control unit 103. As described above, the various processors includes, in addition to the CPUs 52 and 82, which are general-purpose processors that execute software (operation programs 55 and 90) to function as the various processing units, a programmable logic device (PLD), which is a processor of which a circuit configuration can be changed after the manufacturing, such as a field programmable gate array (FPGA), a dedicated electric circuit, which is a processor having a circuit configuration designed specially for executing specific processing, such as an application specific integrated circuit (ASIC), and the like.

One processing unit may be composed of one of various processors described above or may be composed of a combination of two or more processors (for example, a combination of a plurality of FPGAs and/or a combination of a CPU and an FPGA) of the same type or different types. In addition, a plurality of the processing units may be composed of one processor.

As an example in which the plurality of processing units are composed of one processor, first, as represented by a computer, such as a client and a server, there is a form in which one processor is composed of a combination of one or more CPUs and software and the processor functions as the plurality of processing units. Second, as represented by a system on chip (SoC) and the like, there is a form in which a processor that realizes the functions of the entire system including a plurality of processing units with a single integrated circuit (IC) chip is used. As described above, various processing units are composed of using one or more of the various processors as a hardware structure.

Further, as the hardware structure of these various processors, more specifically, it is possible to use an electrical circuit (circuitry) in which circuit elements, such as semiconductor elements, are combined.

From the above description, the invention described in the following supplementary note 1 can be grasped.

[Supplementary Note 1]

A control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the control device comprising an acquisition processor that acquires positional information indicating a position of the observation target, a setting processor that sets, from among the plurality of irradiation positions, a required irradiation position, which is an irradiation position corresponding to the position of the observation target indicated by the positional information and is an irradiation position required for obtaining a plurality of the interference fringe images that are sources of a super-resolution interference fringe image having a resolution exceeding a resolution of the imaging element, a light source control processor that emits the illumination light from the required irradiation position by controlling an operation of the light source, and an imaging control processor that outputs the interference fringe image from the imaging element at each required irradiation position.

In the technology of the present disclosure, it is possible to appropriately combine various embodiments and various modification examples described above. In addition, it is needless to say that the present disclosure is not limited to each of the embodiments described above, various configurations can be adopted as long as the configuration does not deviate from the gist. Further, the technology of the present disclosure includes, in addition to the program, a storage medium that stores the program in a non-transitory manner.

The contents described and shown above are the detailed description of the parts relating to the technology of the present disclosure, and are merely an example of the technology of the present disclosure. For example, the above description of the configuration, the function, the action, and the effect are the description of examples of the configuration, the function, the action, and the effect of the parts relating to the technology of the present disclosure. Therefore, it is needless to say that unnecessary parts may be deleted, new elements may be added, or replacements may be made with respect to the contents described and shown above within a range that does not deviate from the gist of the technology of the present disclosure. In addition, in order to avoid complications and facilitate understanding of the parts relating to the technology of the present disclosure, in the contents described and shown above, the description of technical general knowledge and the like that do not particularly require description for enabling the implementation of the technology of the present disclosure are omitted.

In the present specification, "A and/or B" is synonymous with "at least one of A or B". That is, "A and/or B" means that it may be only A, only B, or a combination of A and B. In addition, in the present specification, in a case in which three or more matters are associated and expressed by "and/or", the same concept as "A and/or B" is applied.

All documents, patent applications, and technical standards mentioned in the present specification are incorporated herein by reference to the same extent as in a case in which each document, each patent application, and each technical standard are specifically and individually described by being incorporated by reference.

What is claimed is:

1. A control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the control device comprising a processor that is configured to:

acquire positional information indicating a position of the observation target;

set, from among the plurality of irradiation positions, a required irradiation position, which is an irradiation position required for obtaining a plurality of the interference fringe images that are sources of a super-resolution interference fringe image having a resolution exceeding a resolution of the imaging element, as a subset of the plurality of irradiation positions corresponding to a region that includes the position of the observation target indicated by the positional information, using a correspondence table indicating correspondences between different regions that include the position of the observation target and different subsets of the plurality of irradiation positions comprising variable number of irradiation positions;

cause the light source to emit the illumination light from the required irradiation position by controlling an operation of the light source; and cause the imaging element to output the interference fringe image at each required irradiation position.

2. The control device according to claim 1,
wherein the light source has a configuration in which a plurality of light emission units of the illumination light are arranged at the plurality of irradiation positions, and
the processor causes the light emission unit corresponding to the required irradiation position to emit the illumination light.

3. The control device according to claim 1,
wherein the light source includes at least one light emission unit of the illumination light and a moving mechanism of the light emission unit, and
the processor causes the light emission unit to emit the illumination light while moving the light emission unit to the required irradiation position by the moving mechanism.

4. The control device according to claim 1,
wherein the processor acquire the positional information by detecting the position of the observation target from a standard interference fringe image, which is the interference fringe image obtained by emitting the illumination light from one preset standard irradiation position among the plurality of irradiation positions, or a standard reconstructed image, which is a reconstructed image representing any tomographic plane of the observation target and is a reconstructed image generated based on the standard interference fringe image.

5. The control device according to claim 1, further comprising:
wherein the processor perform a control of displaying a display screen of a standard interference fringe image, which is the interference fringe image obtained by emitting the illumination light from one preset standard irradiation position among the plurality of irradiation positions, or a display screen of a standard reconstructed image, which is a reconstructed image representing any tomographic plane of the observation target and is a reconstructed image generated based on the standard interference fringe image, and
acquire the positional information by receiving designation of the position of the observation target on the display screen.

6. The control device according to claim 1,
wherein the processor acquire size information indicating a size of the observation target, in addition to the positional information, and
change the number of the required irradiation positions in accordance with the size information.

7. The control device according to claim 1,
wherein, in a case in which a plurality of the observation targets are present and the required irradiation positions of the plurality of observation targets overlap, the processor causes the light source to emit the illumination light only once from overlapping required irradiation positions.

8. The control device according to claim 1,
wherein the observation target is a cell in culture.

9. The control device according to claim 1,
wherein the illumination light is coherent light.

10. An operation method of a control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the operation method comprising:

acquiring positional information indicating a position of the observation target;

setting, from among the plurality of irradiation positions, a required irradiation position, which is an irradiation position required for obtaining a plurality of the interference fringe images that are sources of a super-resolution interference fringe image having a resolution exceeding a resolution of the imaging element, as a subset of the plurality of irradiation positions corresponding to a region that includes the position of the observation target indicated by the positional information, using a correspondence table indicating correspondences between different regions that include the position of the observation target and different subsets of the plurality of irradiation positions comprising variable number of irradiation positions;

causing the light source to emit the illumination light from the required irradiation position by controlling an operation of the light source; and causing the imaging element to output the interference fringe image at each required irradiation position.

11. A non-transitory computer-readable storage medium storing an operation program of a control device of an imaging apparatus including a light source and an imaging element, in which the light source is able to irradiate an observation target with illumination light from a plurality of irradiation positions having different irradiation angles, and the imaging element outputs an interference fringe image by imaging an interference fringe between diffracted light, which is the illumination light diffracted by the observation target, and reference light, which is the illumination light that does not pass through the observation target, the operation program causing a computer to function as:

acquire positional information indicating a position of the observation target;

set, from among the plurality of irradiation positions, a required irradiation position, which is an irradiation position required for obtaining a plurality of the interference fringe images that are sources of a super-resolution interference fringe image having a resolution exceeding a resolution of the imaging element, as a subset of the plurality of irradiation positions corresponding to a region that includes the position of the observation target indicated by the positional information, using a correspondence table indicating correspondences between different regions that include the position of the observation target and different subsets of the plurality of irradiation positions comprising variable number of irradiation positions;

cause the light source to emit the illumination light from the required irradiation position by controlling an operation of the light source; and cause the imaging element to output the interference fringe image at each required irradiation position.

* * * * *